US010653301B2

(12) United States Patent
Iguchi et al.

(10) Patent No.: US 10,653,301 B2
(45) Date of Patent: May 19, 2020

(54) OPTICAL UNIT AND ENDOSCOPE

(71) Applicant: OLYMPUS CORPORATION, Tokyo (JP)

(72) Inventors: Takehiko Iguchi, Hino (JP); Takeshi Saito, Tokorozawa (JP); Sho Nakamura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 363 days.

(21) Appl. No.: 15/730,926

(22) Filed: Oct. 12, 2017

(65) Prior Publication Data
US 2018/0049621 A1 Feb. 22, 2018

Related U.S. Application Data

(63) Continuation of application No. PCT/JP2015/061639, filed on Apr. 15, 2015.

(51) Int. Cl.
*A61B 1/00* (2006.01)
*G02B 23/24* (2006.01)
*H04N 5/225* (2006.01)

(52) U.S. Cl.
CPC ........ *A61B 1/0019* (2013.01); *A61B 1/00096* (2013.01); *G02B 23/243* (2013.01); *A61B 1/00009* (2013.01); *H04N 2005/2255* (2013.01)

(58) Field of Classification Search
CPC ............ A61B 1/00096; A61B 1/00158; G02B 23/2438; G02B 7/08; G02B 23/2476; G02B 7/09
See application file for complete search history.

(56) References Cited

U.S. PATENT DOCUMENTS 5,541,777 A * 7/1996 Sakamoto ............... G02B 7/102
310/13
6,099,467 A * 8/2000 Kehr ................... A61B 1/00188
359/822
(Continued)

FOREIGN PATENT DOCUMENTS

CN 102314046 A 1/2012
JP S57-108806 A 7/1982
(Continued)

OTHER PUBLICATIONS

Japanese Office Action dated Oct. 8, 2019 in Japanese Patent Application No. 2017-512141.
(Continued)

*Primary Examiner* — Timothy J Neal
*Assistant Examiner* — Jae Woo
(74) *Attorney, Agent, or Firm* — Scully, Scott, Murphy & Presser, P.C.

(57) ABSTRACT

An optical unit includes: a fixed portion configured to hold at least one of an object side fixed lens group and an image side fixed lens group; a movable portion configured to hold a movable lens group between the object side fixed lens group and the image side fixed lens group; and a voice coil motor configured to relatively move the movable portion with respect to the fixed portion in a direction of a central axis, the voice coil motor including a coil arranged on the fixed portion, and magnets magnetically polarized in directions orthogonal to the central axis and substantially symmetrical with respect to the central axis. At least two magnets adjacent to each other in a circumferential direction in a cross section orthogonal to the central axis are arranged so as to be shifted in opposite directions in a circumferential direction.

11 Claims, 26 Drawing Sheets

(56) References Cited

U.S. PATENT DOCUMENTS

| | | | |
|---|---|---|---|
| 9,448,397 B2* | 9/2016 | Makiyama | A61B 1/00096 |
| 9,924,854 B2* | 3/2018 | Iwasaki | A61B 1/00 |
| 10,120,181 B2* | 11/2018 | Kono | A61B 1/00096 |
| 10,244,932 B2* | 4/2019 | Fujii | G02B 23/2438 |
| 10,278,565 B2* | 5/2019 | Wieters | A61B 1/00071 |
| 10,459,192 B2* | 10/2019 | Kono | G02B 23/2438 |
| 2006/0138873 A1 | 6/2006 | Yasuda | |
| 2008/0272869 A1* | 11/2008 | Takayama | A61B 1/00188 335/219 |
| 2009/0015948 A1* | 1/2009 | Wada | G02B 7/08 359/824 |
| 2009/0073585 A1* | 3/2009 | Yamashita | G02B 7/022 359/824 |
| 2010/0328791 A1* | 12/2010 | Jung | G03B 17/02 359/824 |
| 2011/0210689 A1* | 9/2011 | Vogel | A61B 1/0016 318/631 |
| 2011/0267712 A1* | 11/2011 | Umeda | G03B 5/02 359/823 |
| 2012/0002102 A1 | 1/2012 | Sekimoto | |
| 2012/0063005 A1* | 3/2012 | Aoshima | G03B 9/06 359/699 |
| 2013/0314517 A1* | 11/2013 | Makiyama | A61B 1/045 348/65 |
| 2015/0287508 A1* | 10/2015 | Wieters | A61B 17/00 335/253 |
| 2016/0018625 A1* | 1/2016 | Morishima | G02B 7/04 359/824 |
| 2016/0041381 A1* | 2/2016 | Makiyama | A61B 1/00096 359/824 |
| 2016/0282601 A1* | 9/2016 | Kono | A61B 1/05 |
| 2016/0374543 A1* | 12/2016 | Wieters | A61B 1/00071 600/167 |

FOREIGN PATENT DOCUMENTS

| | | |
|---|---|---|
| JP | H02-301023 A | 12/1990 |
| JP | H07-199027 A | 8/1995 |
| JP | H08-086949 A | 4/1996 |
| JP | 2006-091207 A | 4/2006 |
| JP | 2006-178291 A | 7/2006 |
| JP | 2007057650 A | 3/2007 |
| JP | 3142643 U | 6/2008 |
| JP | 2009-160276 A | 7/2009 |
| JP | 2010-243195 A | 10/2010 |
| JP | 2011-257705 A | 12/2011 |
| JP | 2012-032778 A | 2/2012 |
| JP | 2014-197112 A | 10/2014 |

OTHER PUBLICATIONS

International Search Report dated Jul. 21, 2015 issued in PCT/JP2015/061639.

* cited by examiner

OPTICAL UNIT AND ENDOSCOPE

This application is a continuation of PCT International Application No. PCT/JP2015/061639 filed on Apr. 15, 2015, which designates the United States, incorporated herein by reference.

BACKGROUND

The present disclosure relates to an optical unit and an endoscope.

In the related art, an endoscope including a movable lens frame to which a lens is attached and having a zoom function for changing imaging magnification by moving forward and backward the movable lens frame is disclosed (for example, refer to JP 2010-243195 A).

SUMMARY

An optical unit may include: a fixed portion having a tubular shape configured to hold at least one of an object side fixed lens group and an image side fixed lens group, the fixed portion including a plurality of thinned portions formed, at a regular interval, at positions symmetrical with respect to a central axis of the tubular shape; a movable portion having a tubular shape configured to hold a movable lens group between the object side fixed lens group and the image side fixed lens group, the movable portion being arranged radially inside the fixed portion so as to be slidable with respect to the fixed portion and having a same central axis as the fixed portion; and a voice coil motor configured to relatively move the movable portion with respect to the fixed portion in a direction of the central axis, the voice coil motor including a coil arranged on the fixed portion, and a plurality of magnets arranged on the movable portion so as to be accommodated in the thinned portions of the fixed portion, respectively, the magnets being magnetically polarized in directions orthogonal to the central axis and substantially symmetrical with respect to the central axis, and at least two magnets adjacent to each other in a circumferential direction in a cross section orthogonal to the central axis out of the plurality of magnets are arranged so as to be shifted in opposite directions in the circumferential direction.

The above and other objects, features, advantages and technical and industrial significance of this disclosure will be better understood by reading the following detailed description of presently preferred embodiments of the disclosure, when considered in connection with the accompanying drawings.

DETAILED DESCRIPTION

A mode for carrying out the present disclosure (hereinafter, referred to as an "embodiment") is hereinafter described.

First Embodiment

Figure 1:
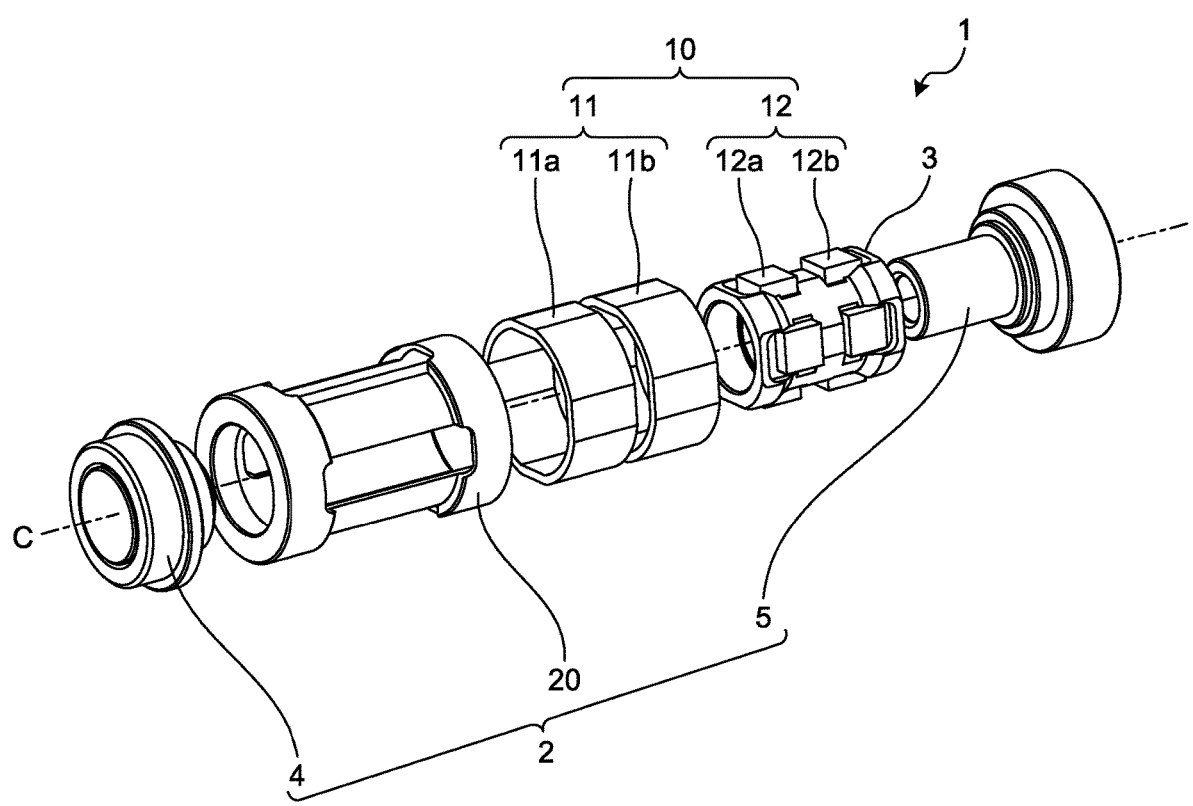
FIG. 1 is an exploded perspective view illustrating a configuration of an optical unit according to a first embodiment.
Figure 2:
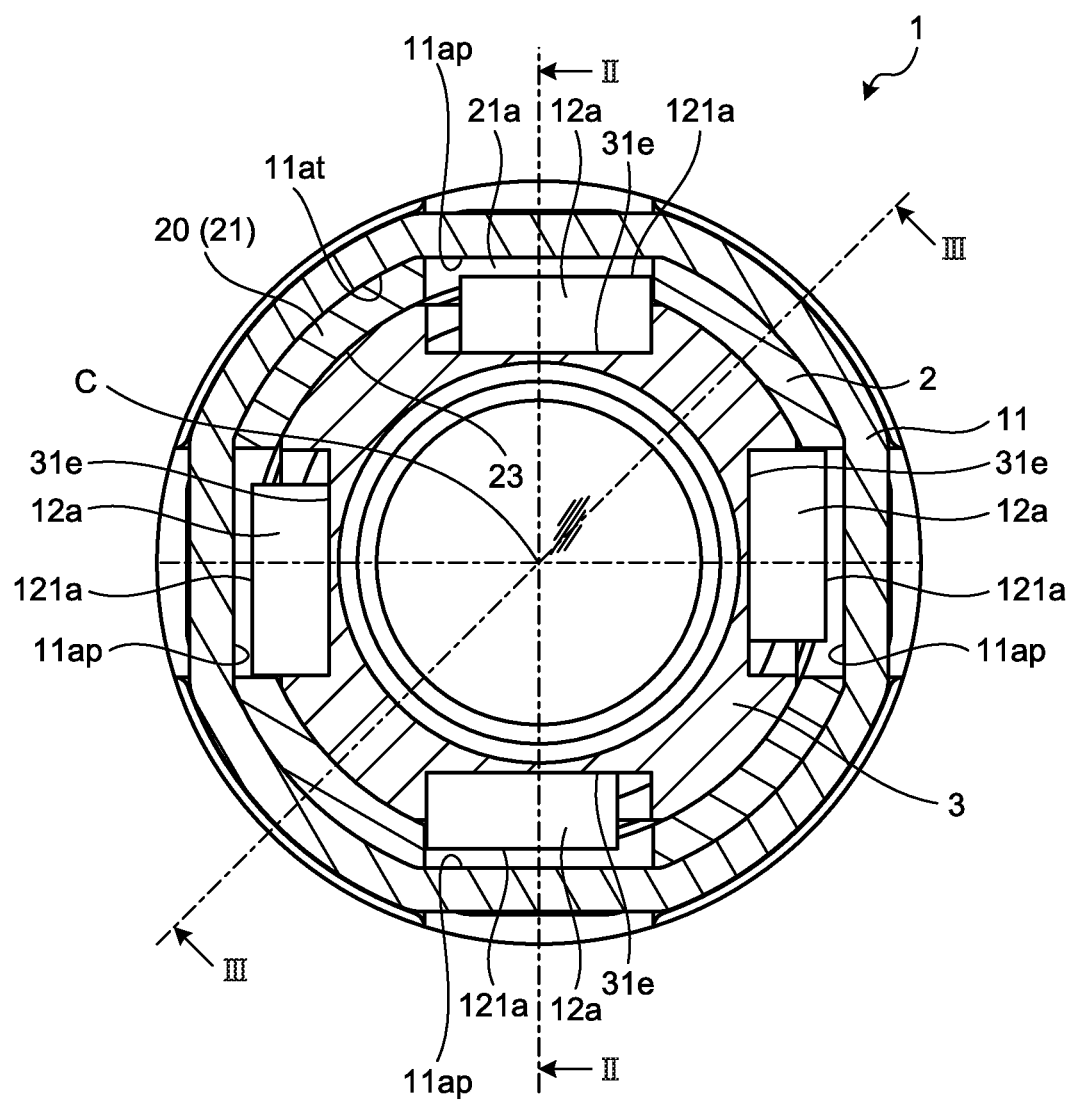
FIG. 2 is a cross-sectional view illustrating a configuration of a substantial part of the optical unit according to the first embodiment.
Figure 3:
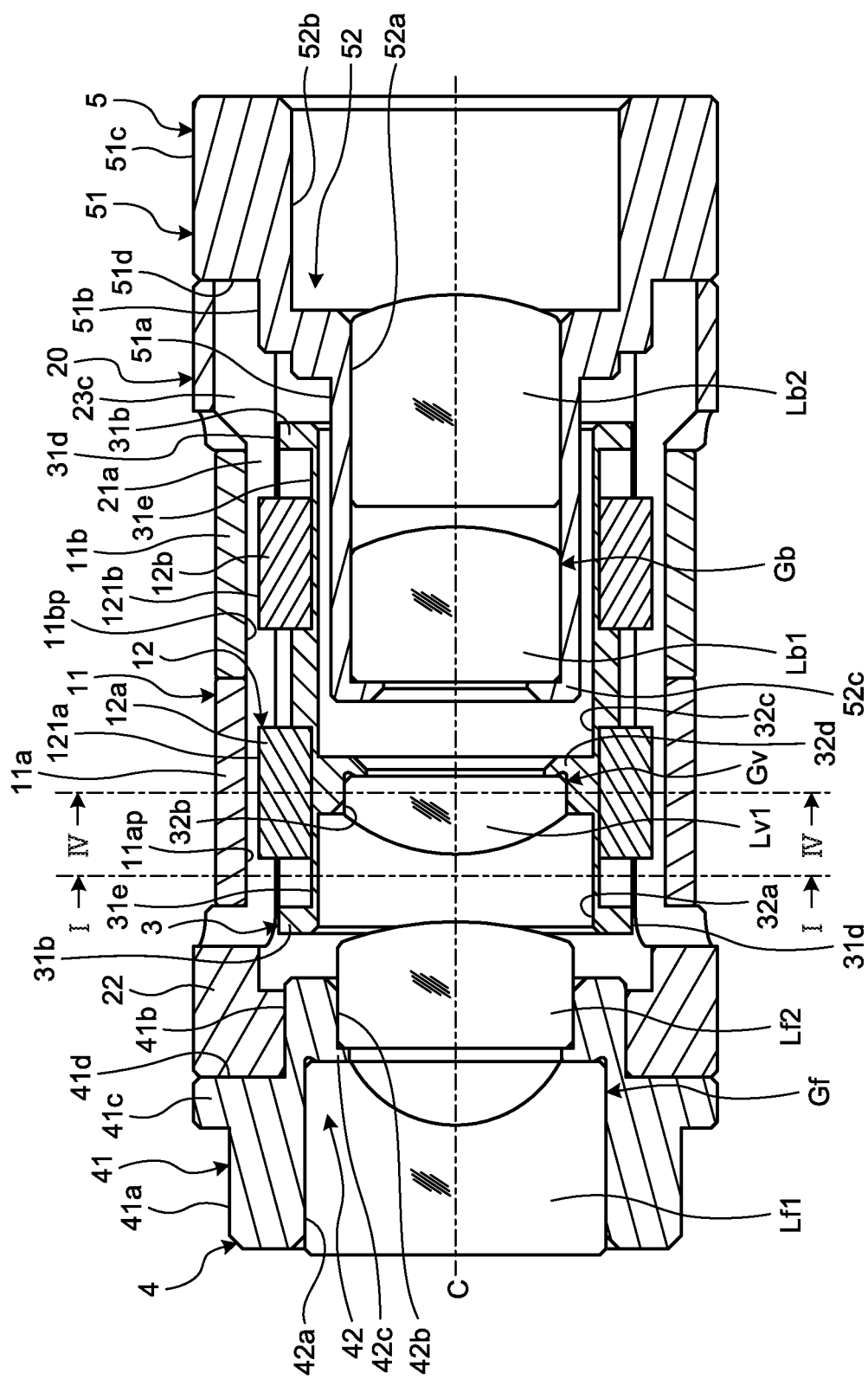
FIG. 3 is a cross-sectional view of the optical unit as seen in a cross section taken along line II-II of FIG. 2.
Figure 4:
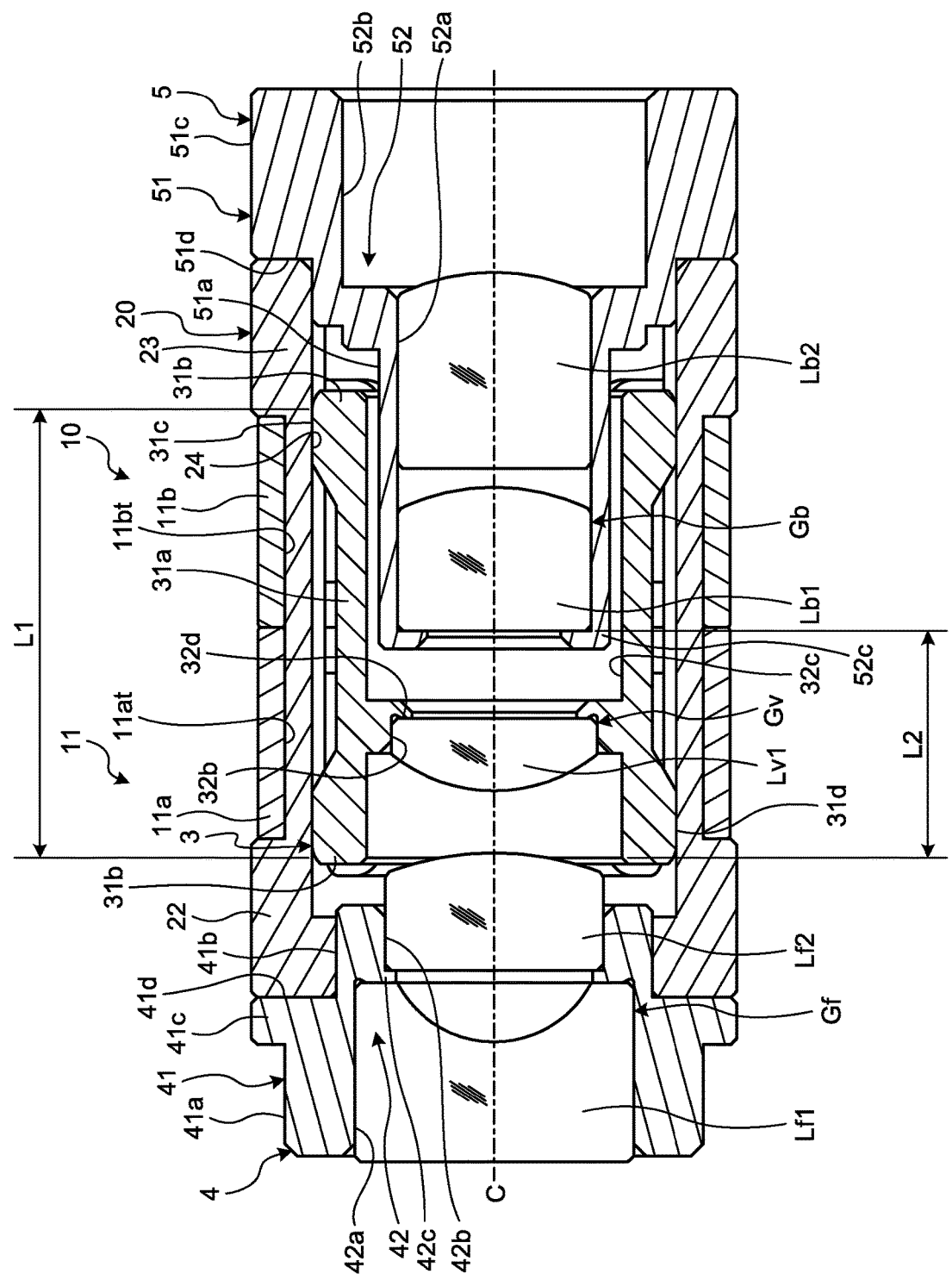
FIG. 4 is a cross-sectional view of the optical unit as seen in a cross section taken along line III-III of FIG. 2.

FIG. 1 is an exploded perspective view illustrating a configuration of an optical unit according to a first embodiment. FIG. 2 is a cross-sectional view illustrating a configuration of a substantial part of the optical unit according to the first embodiment. FIG. 3 is a cross-sectional view of the optical unit as seen in a cross section taken along line II-II of FIG. 2. FIG. 4 is a cross-sectional view of the optical unit as seen in a cross section taken along line III-III of FIG. 2. Meanwhile, FIG. 2 also is a cross-sectional view of the optical unit as seen in a cross section taken along line I-I of FIG. 3.

An optical unit 1 illustrated in FIGS. 1 to 4 is provided with a fixed portion 2, a movable portion 3 movable with respect to the fixed portion 2, and a voice coil motor 10 that generates driving force for moving the movable portion 3 with respect to the fixed portion 2.

The fixed portion 2 includes a fixed portion main body 20, a front frame portion 4 attached to an object side of the fixed portion main body 20 that holds an object side fixed lens group Gf on a side closer to an object than a movable lens group Gv held by the movable portion 3, and a back frame portion 5 attached to an image side of the fixed portion main body 20 that holds an image side fixed lens group Gb on a side closer to an image than the movable lens group Gv.

Figure 5:
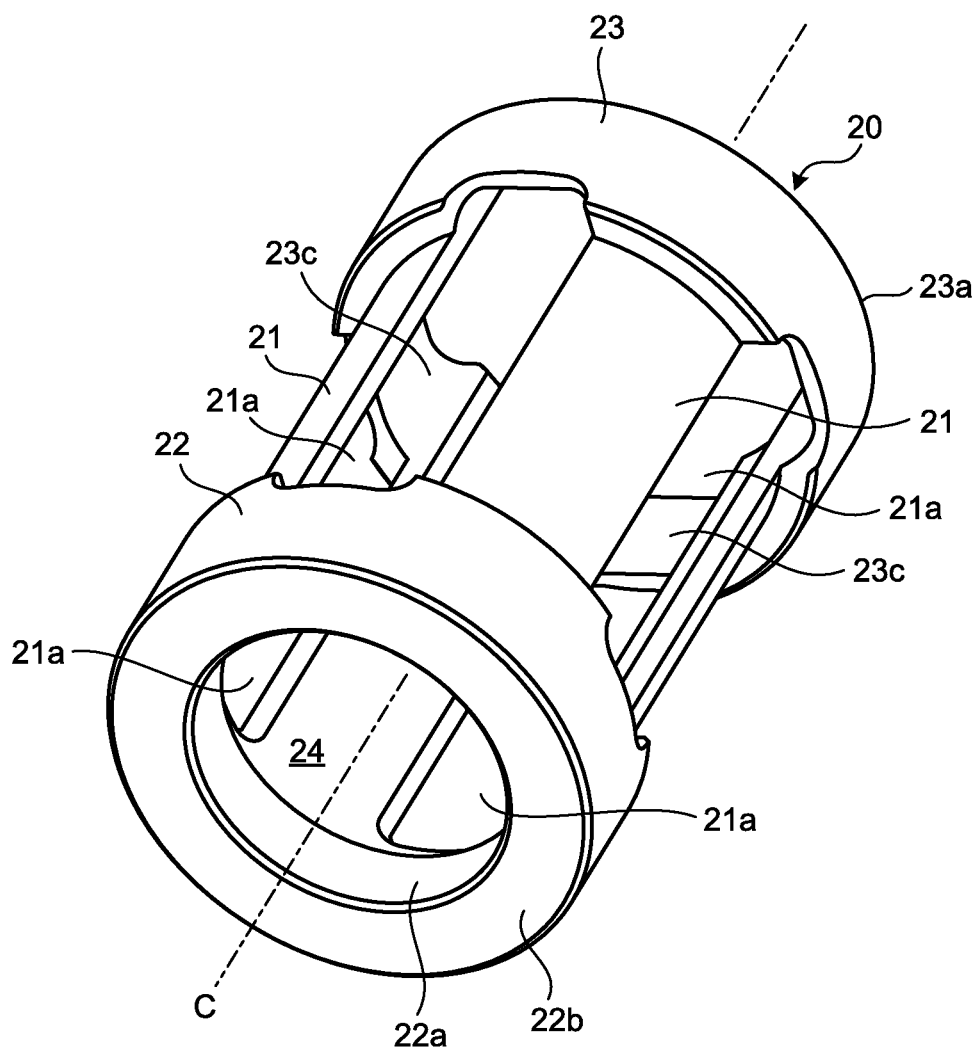
FIG. 5 is a perspective view illustrating a configuration of a fixed portion main body of the optical unit according to the first embodiment.

FIG. 5 is a perspective view illustrating a configuration of the fixed portion main body 20. The fixed portion main body 20 illustrated in this drawing is formed of a tubular member centered around a predetermined axis C. The fixed portion main body 20 includes a tubular portion 21 having the axis C as a central axis, an object side thick portion 22 formed on the object side in an axis C direction with respect to the tubular portion 21, and an image side thick portion 23 formed on a side opposite to the object side thick portion 22 in the axis C direction across the tubular portion 21. The fixed portion main body 20 has 90-degree rotational symmetry with respect to the axis C. Hereinafter, the side opposite to the object side in the axis C direction is referred to as the image side.

A thinned portion 21a is formed in the tubular portion 21. Specifically, four thinned portions 21a penetrating in a radial direction of the tubular portion 21 are formed at 90-degree interval in a circumferential direction with respect to the central axis C in a longitudinal direction of the tubular portion 21. A radially inner surface of the tubular portion 21 except the thinned portions 21a is a tubular cylindrical surface and serves as a fixed side sliding surface 24 for guiding and supporting the movable portion 3. The fixed side sliding surface 24 has a shape divided in the circumferential direction by the thinned portions 21a.

The object side thick portion 22 is formed to project radially outward and radially inward from the tubular portion 21. The image side thick portion 23 is formed to project radially outward from the tubular portion 21. A groove 23c is formed on the fixed side sliding surface 24 on a radially inner side of the image side thick portion 23. When the movable portion 3 is assembled, a magnet 12 to be described later passes through the groove 23c. Therefore, it becomes possible to smoothly assemble the movable portion 3 with respect to the fixed portion main body 20. Meanwhile, a structure may be such that the object side thick portion 22 and the image side thick portion 23 are formed separately from the tubular portion 21 to be attached to the tubular portion 21 at the time of assembly.

Figure 6A:
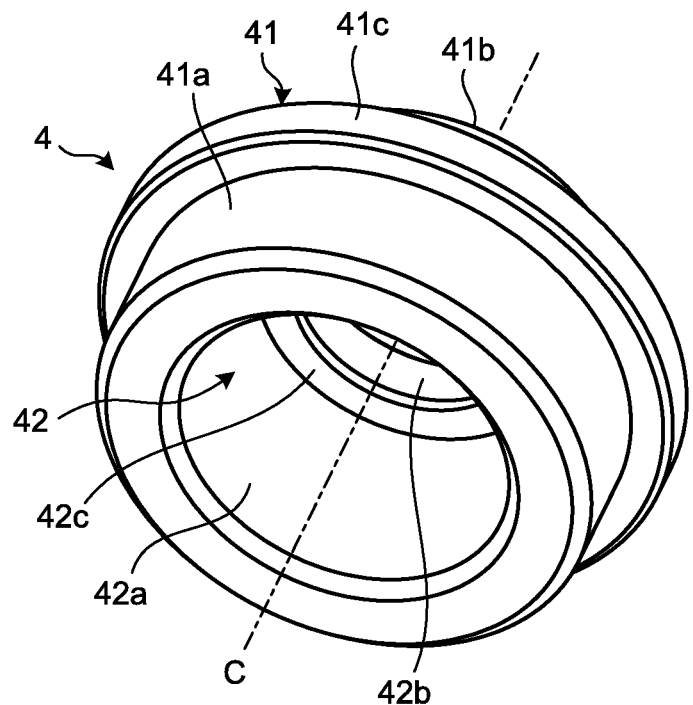
FIG. 6A is a perspective view illustrating a configuration of a front frame portion of the optical unit according to the first embodiment.
Figure 6B:
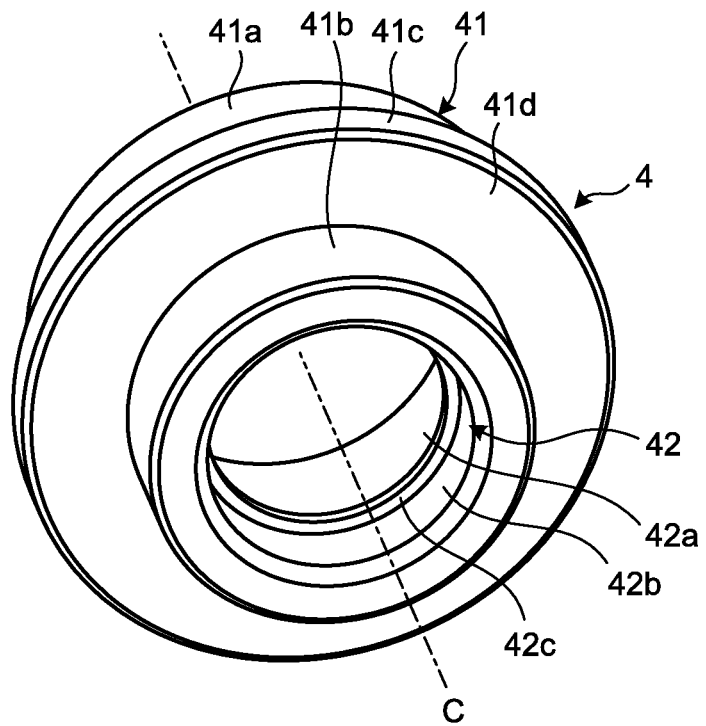
FIG. 6B is a perspective view illustrating a configuration when the front frame portion of the optical unit according to the first embodiment is seen from a side opposite to FIG. 6A.

FIGS. 6A and 6B are perspective views illustrating a configuration of the front frame portion 4, the perspective views when this is seen from different sides of the axis C. Meanwhile, a central axis of the front frame portion 4 is referred to as the axis C because this coincides with the central axis of the fixed portion main body 20 at the time of assembly. The front frame portion 4 is a tubular member including an outer peripheral portion 41 and an inner peripheral portion 42. The outer peripheral portion 41 includes a first outer peripheral portion 41a, a second outer peripheral portion 41b, and an outer peripheral side convex portion 41c. The inner peripheral portion 42 includes a first inner peripheral portion 42a, a second inner peripheral portion 42b, and an inner peripheral side convex portion 42c.

In the outer peripheral portion 41, the first outer peripheral portion 41a is larger in diameter than the second outer peripheral portion 41b. The outer peripheral side convex portion 41c having the largest diameter projecting radially outward is provided between the first outer peripheral portion 41a and the second outer peripheral portion 41b.

In the inner peripheral portion 42, the first inner peripheral portion 42a is larger in diameter than the second inner peripheral portion 42b. The inner peripheral side convex portion 42c having the smallest diameter projecting radially inward is located between the first inner peripheral portion 42a and the second inner peripheral portion 42b.

The front frame portion 4 holds the object side fixed lens group Gf. The object side fixed lens group Gf includes a front first lens Lf1 and a front second lens Lf2 arranged in this order from the object side. The first inner peripheral portion 42a holds the front first lens Lf1 and the second inner peripheral portion 42b holds the front second lens Lf2. The image side of the front first lens Lf1 and the object side of the front second lens Lf2 preferably abut the inner peripheral side convex portion 42c as illustrated in FIGS. 3 and 4.

When the front frame portion 4 is inserted into the fixed portion main body 20, the former is inserted into the latter until an end face 22b on the object side of the fixed portion main body 20 comes into contact with a step portion 41d between the second outer peripheral portion 41b and the outer peripheral side convex portion 41c while the second outer peripheral portion 41b is brought into contact with an inner peripheral surface 22a of the object side thick portion 22 of the fixed portion main body 20.

Figure 7A:
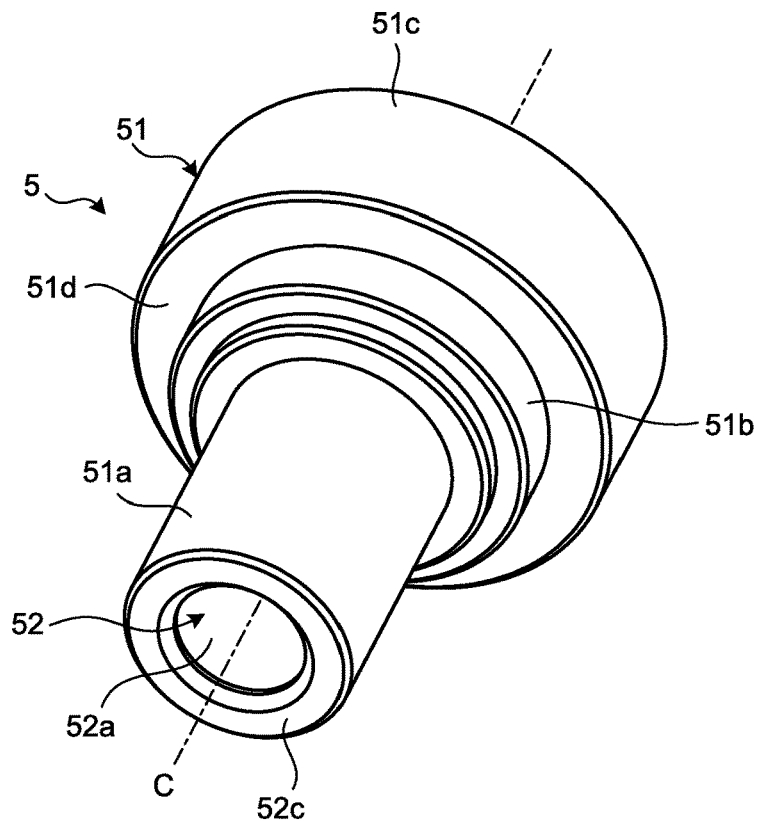
FIG. 7A is a perspective view illustrating a configuration of a back frame portion of the optical unit according to the first embodiment.
Figure 7B:
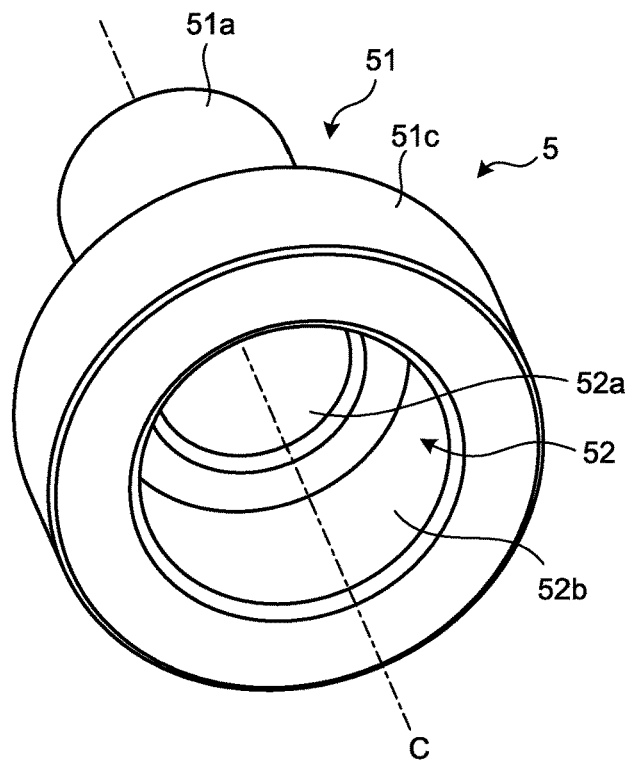
FIG. 7B is a perspective view illustrating a configuration when the back frame portion of the optical unit according to the first embodiment is seen from a side opposite to FIG. 7A

FIGS. 7A and 7B are perspective views illustrating a configuration of the back frame portion 5, the perspective views when this is seen from the different sides of the axis C. Meanwhile, a central axis of the back frame portion 5 is referred to as the axis C because this coincides with the central axis of the fixed portion main body 20 at the time of assembly as the front frame portion 4. The back frame portion 5 is a tubular member including an outer peripheral portion 51 and an inner peripheral portion 52. The outer peripheral portion 51 includes a first outer peripheral portion 51a, a second outer peripheral portion 51b, and third outer peripheral portion 51c. The inner peripheral portion 52 includes a first inner peripheral portion 52a, a second inner peripheral portion 52b, and an inner peripheral side convex portion 52c.

In the outer peripheral portion 51, the first outer peripheral portion 51a is smaller in diameter than the second outer peripheral portion 51b, and the second outer peripheral portion 51b is smaller in diameter than the third outer peripheral portion 51c.

In the inner peripheral portion 52, the first inner peripheral portion 52a is smaller in diameter than the second inner peripheral portion 52b. The inner peripheral side convex portion 52c having the smallest diameter projecting radially inward is provided on an end portion on the object side of the first inner peripheral portion 52a.

The back frame portion 5 holds the image side fixed lens group Gb. The image side fixed lens group Gb includes a back first lens Lb1 and a back second lens Lb2. The first inner peripheral portion 52a holds the back first lens Lb1 and the back second lens Lb2 in this order from the object side. The object side of the back first lens Lb1 preferably abuts the inner peripheral side convex portion 52c as illustrated in FIGS. 3 and 4.

When the back frame portion 5 is inserted into the fixed portion main body 20, the former is inserted into the latter until an end face 23a on the image side of the fixed portion main body 20 comes into contact with a step portion 51d between the second outer peripheral portion 51b and the third outer peripheral portion 51c while the second outer peripheral portion 51b is brought into contact with the fixed side sliding surface 24 of the image side thick portion 23 of the fixed portion main body 20.

The fixed portion 2 having the above-described configuration is formed of, for example, a non-magnetic material having relative magnetic permeability larger than 1.0. Austenitic stainless steel and the like may be mentioned, for example, as such a material.

Figure 8:
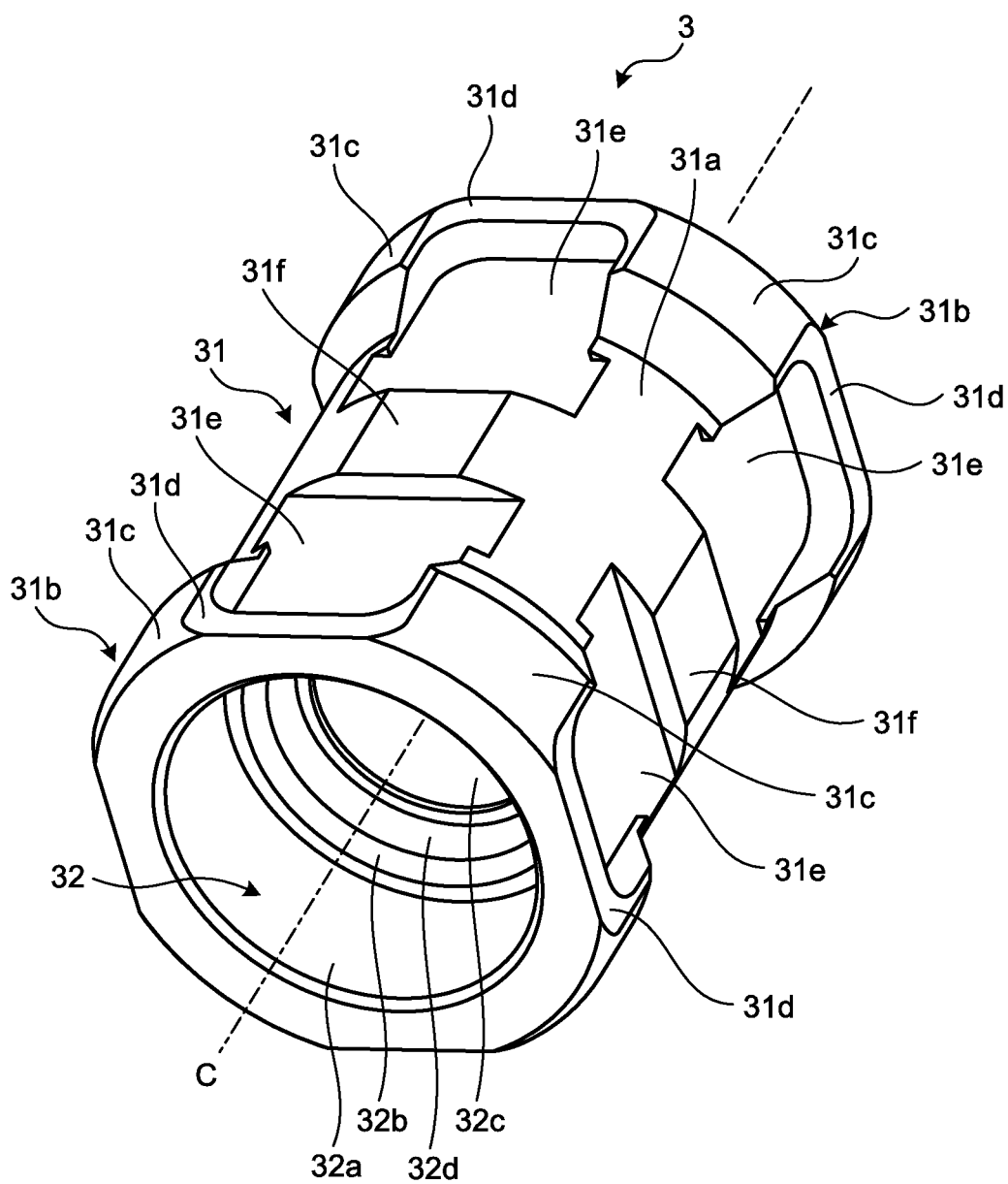
FIG. 8 is a perspective view illustrating a configuration of a movable portion of the optical unit according to the first embodiment.

FIG. 8 is a perspective view illustrating a configuration of the movable portion 3. The movable portion 3 illustrated in this drawing is formed of a tubular member including an outer peripheral portion 31 and an inner peripheral portion 32. Hereinafter, a central axis of the movable portion 3 is also referred to as the axis C. This is because the central axis of the movable portion 3 coincides with the central axis of the fixed portion main body 20 at the time of assembly.

The outer peripheral portion 31 includes a tubular portion 31a and two projecting edge portions 31b formed on both end portions in the axis C direction of the tubular portion 31a each having a larger outer peripheral diameter than that of the tubular portion 31a. The tubular portion 31a and the projecting edge portion 31b may be formed as an integral member or as separate members.

The projecting edge portion 31b includes a movable side sliding surface 31c formed of an outer peripheral surface thereof and a planar portion 31d formed on a part of a radially outer side of the projecting edge portion 31b. In a case illustrated in FIG. 8, the projecting edge portion 31b includes four movable side sliding surfaces 31c and four planar portions 31d alternately in a circumferential direction around the axis C at a regular interval. The planar portion 31d passes through the same plane as any of the four planar portions 31d formed on the other end side in the axis C direction. In other words, the outer peripheral portion 31 includes four groups of the two planar portions 31d formed on different end portions and passing through the same plane.

A step portion 31e formed radially inside the tubular portion 31a including a planar outer peripheral surface is provided between each of the four groups of the planar portions 31d. At the center in the axis C direction of the step portion 31e formed between each of the four groups of the planar portions 31d, a cutout portion 31f having a planar outer periphery obtained by cutting out a surface of the tubular portion 31a is provided.

The inner peripheral portion 32 includes a first inner peripheral portion 32a, a second inner peripheral portion 32b, a third inner peripheral portion 32c, and an inner peripheral side convex portion 32d. The second inner peripheral portion 32b is smaller in diameter than the first inner peripheral portion 32a and the third inner peripheral portion 32c. The inner peripheral side convex portion 32d having the smallest diameter projecting radially inward is provided between the second inner peripheral portion 32b and the third inner peripheral portion 32c.

The movable portion 3 holds the movable lens group Gv. Specifically, the second inner peripheral portion 32b of the movable portion 3 holds the movable first lens Lv1 included in the movable lens group Gv. As illustrated in FIGS. 3 and 4, the image side of the movable first lens Lv1 preferably abuts the inner peripheral side convex portion 32d.

The movable portion 3 is inserted into the fixed portion main body 20 while the movable side sliding surface 31c is in contact with the fixed side sliding surface 24. Also, as illustrated in FIGS. 3 and 4, the former is inserted into the latter such that a radially inner side of the third inner peripheral portion 32c is opposed to the first outer peripheral portion 51a of the back frame portion 5. According to this, at least a part of the image side fixed lens group Gb is present on the radially inner side of the third inner peripheral portion 32c of the movable portion 3. In the first embodiment, when the movable portion 3 moves so as to be the closest to the object, at least a part of the object side fixed lens group Gf is present on the radially inner side of the first inner peripheral portion 32a of the movable portion 3.

The movable portion 3 having the above-described configuration is formed of a material such as stainless steel, aluminum, resin or the like, for example.

In the optical unit 1, as illustrated in FIG. 4, in the direction along the axis C, a distance L1 from a position the closest to object to a position the closest to the image on the movable side sliding surface 31c of the movable portion 3 is longer than a distance L2 from an emission surface of the object side fixed lens group Gf held by the front frame portion 4 to an incident surface of the image side fixed lens group Gb held by the back frame portion 5 (L1>L2). Meanwhile, the distance from the position the closest to the object to the position the closest to the image on the movable side sliding surface 31c of the movable portion 3 does not include a chamfered portion.

Next, a configuration of the voice coil motor 10 is described. As illustrated in FIG. 3, the voice coil motor 10 includes a coil 11 arranged on the fixed portion main body 20 of the fixed portion 2 and the magnet 12 arranged on the movable portion 3 so as to be opposed to the coil 11.

As illustrated in FIGS. 3 and 4, the coil 11 includes a first coil 11a wound around an outer periphery of the tubular portion 21 of the fixed portion main body 20 and a second coil 11b arranged side by side with the first coil 11a in the axis C direction wound around the outer periphery of the tubular portion 21 of the fixed portion main body 20. Meanwhile, the coil 11 wound in advance may be arranged later. The first coil 11a and the second coil 11b adjacent to each other in the axis C direction are preferably connected in series, but they may also be connected in parallel.

As illustrated in FIGS. 3 and 4, the first coil 11*a* and the second coil 11*b* include planar portions 11*ap* and 11*bp* opposed to the thinned portion 21*a* of the fixed portion main body 20, respectively. The first coil 11*a* and the second coil 11*b* also include cylindrical portions 11*at* and 11*bt* opposed to the tubular portion 21, respectively. In the cross section orthogonal to the axis C, four planar portions 11*ap* and four cylindrical portions 11*at* are alternately arranged in the first coil 11*a*. Similarly, in the cross section orthogonal to the axis C, four planar portions 11*bp* and four cylindrical portions 11*bt* are alternately arranged in the second coil 11*b* (refer to FIG. 2).

As the magnet 12, a first magnet 12*a* and a second magnet 12*b* are arranged on the movable portion 3 so as to be accommodated in each thinned portion 21*a* of the fixed portion 2. As illustrated in FIGS. 1 to 4, the magnet 12 includes four first magnets 12*a* and four second magnets 12*b* arranged side by side in the axis C direction so as to be opposed to the planar portions 11*ap* and 11*bp* on an inner side of the planar portion 11*ap* of the first coil 11*a* and the planar portion 11*bp* of the second coil 11*b*, respectively. When the four first magnets 12*a* are seen in the cross section orthogonal to the axis C, intervals between the first magnets 12*a* adjacent in the circumferential direction are not equal, and there are two groups with a smaller interval. Specifically, among the four first magnets 12*a* located on upper, lower, left, and right sides of the axis C in FIG. 2, the interval in the circumferential direction between the first magnet 12*a* located on the upper side of the axis C and the first magnet 12*a* located on the right side, and the interval in the circumferential direction between the first magnet 12*a* located on the left side of the axis C and the first magnet 12*a* located on the lower side in FIG. 2 are smaller than the intervals in the circumferential direction of the other adjacent first magnets 12*a*. In other words, there are two groups of the adjacent first magnets 12*a* arranged so as to be shifted in opposite directions in the circumferential direction in the cross section orthogonal to the axis C. Meanwhile, the arrangement of the four second magnets 12*b* in the cross section orthogonal to the axis C is preferably similar to the arrangement of the first magnets 12*a* illustrated in FIG. 2.

Figure 9:
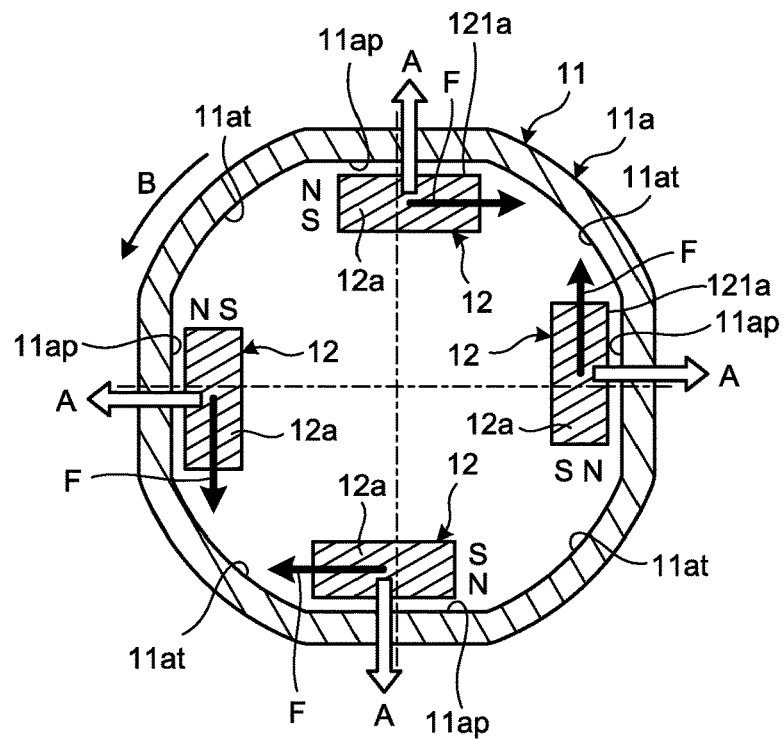
FIG. 9 is a view illustrating a configuration of only a voice coil motor as seen in a cross section taken along line IV-IV of FIG. 3.

FIG. 9 is a view illustrating a configuration of only the voice coil motor as seen in a cross section taken along line IV-IV of FIG. 3. In FIG. 9, black arrow F indicates force (suction force) received by each first magnet 12*a* from the fixed portion 2. In this case, resultant force obtained by combining the suction forces received by the four first magnets 12*a* is substantially zero. The same applies to the four second magnets 12*b*. Therefore, according to the first embodiment, rotational moment around the axis C becomes substantially zero, and frictional force between the fixed portion 2 and the movable portion 3 may be reduced. As a result, since driving efficiency when the movable portion 3 is driven is improved, the voice coil motor 10 may be made compact.

As illustrated in FIGS. 3 and 4, the sum of widths in the axis C direction of the first magnet 12*a* and the second magnet 12*b* is shorter than the sum of widths in the axis C direction of the first coil 11*a* and the second coil 11*b*. According to this, the first magnet 12*a* and the second magnet 12*b* may be always present within the width in the axis C direction of the first coil 11*a* and the second coil 11*b* within a moving range of the movable portion 3.

Figure 10:
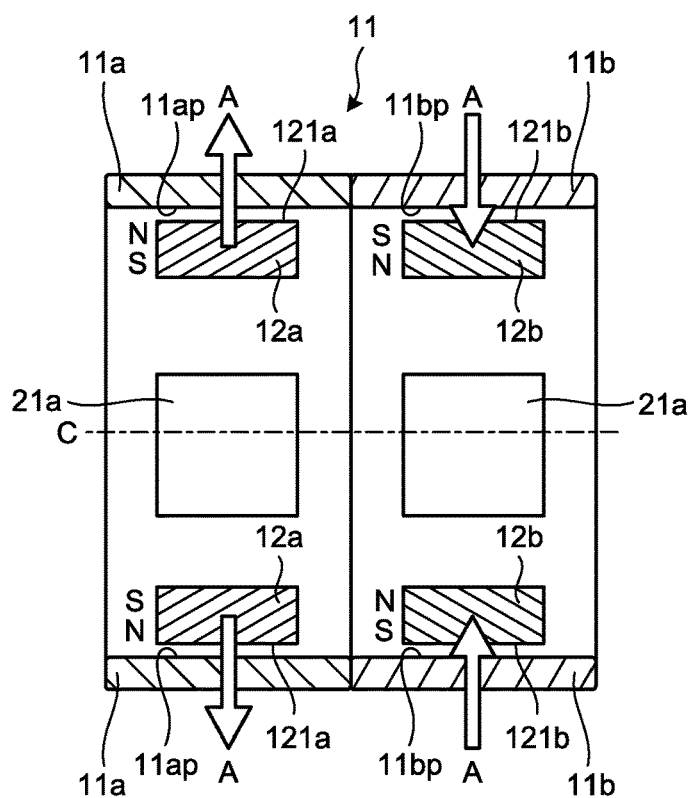
FIG. 10 is a view illustrating only the voice coil motor in the same cross section as FIG. 3.

FIG. 10 is a view illustrating only the voice coil motor in the same cross section as FIG. 3. As illustrated in FIGS. 9 and 10, the first magnet 12*a* and the second magnet 12*b* forming a group in the axis C direction are arranged apart from each other. A group of the first magnets 12*a* and a group of the second magnets 12*b* are magnetized in the radial direction with magnetic poles opposite to each other. In the case illustrated in FIGS. 9 and 10, the first magnet 12*a* has an N pole on a side of the first coil 11*a* and an S pole on the opposite side thereof, and the second magnet 12*b* has an S pole on a side of the second coil 11*b* and an N pole on the opposite side thereof. In this case, magnetic polarization directions of the first magnet 12*a* and the second magnet 12*b* are orthogonal to the axis C as indicated by outline arrows A in FIGS. 9 and 10. Meanwhile, in more general, the magnetic polarization directions of the first magnet 12*a* and the second magnet 12*b* may be the directions intersecting with the axis C.

In the first embodiment, winding directions of the coil 11 are opposed to each other between the group of the first magnets 12*a* and the group of the second magnets 12*b*. For example, when the first coil 11*a* is wound in a direction indicated by arrow B as illustrated in FIG. 9, the second coil 11*b* may be wound in the opposite direction. Alternatively, the winding directions of the first coil 11*a* and the second coil 11*b* may be made the same, and the first coil 11*a* and the second coil 11*b* may be connected to each other so that current directions are opposite to each other. In this case, when current in the direction indicated by arrow B is applied to the first coil 11*a* as illustrated in FIG. 9, the current may flow in the second coil 11*b* in the direction opposite to the direction indicated by arrow B.

In the optical unit 1 having the above-described configuration, the movable portion 3 in which the first magnet 12*a* is installed so as to be opposed to the first coil 11*a* is arranged on the radially inner side of the fixed portion main body 20 around which the first coil 11*a* is wound. Therefore, the planar portion 11*ap* of the first coil 11*a* is present in a magnetic field in a direction orthogonal to a radially outer surface 121*a* of the first magnet 12*a*. Meanwhile, the second magnet 12*b* is configured similarly. Therefore, the driving efficiency is improved and the movable portion 3 may be quickly moved. Also, by making the radially outer surface 121*a* of the first magnet 12*a* and a radially outer surface 121*b* of the second magnet 12*b* planar, it is possible to easily assemble the optical unit 1.

When the current is applied to the coil 11 of the optical unit 1, force in the axis C direction is generated in the movable portion 3 due to an effect of the magnetic field of the magnet 12, and the movable portion 3 moves in the axis C direction with respect to the fixed portion 2. For example, by controlling the current applied to the first coil 11*a* and to the second coil 11*b*, the movable portion 3 may be moved with respect to the fixed portion 2. Even in a state where the movable portion 3 moves with respect to the fixed portion 2, the radially outer surface of the magnet 12 is arranged in the thinned portion 21*a* of the fixed portion main body 20.

Also, in the optical unit 1, as illustrated in FIG. 4, the outer peripheral surface of the projecting edge portion 31*b* of the movable portion 3 forms the movable side sliding surface 31*c* which comes into contact with the fixed side sliding surface 24 of the fixed portion main body 20. By bringing the fixed side sliding surface 24 of the fixed portion main body 20 into contact with the movable side sliding surface 31*c* of the movable portion 3, the movable portion 3 may be moved so as to be always in contact with the fixed portion main body 20, and it is possible to inhibit the movable portion 3 from inclining with respect to the fixed portion 2 and to accurately move the movable portion 3.

According to the first embodiment described above, the voice coil motor 10 including the coil 11 arranged on the fixed portion 2 and the magnet 12 arranged on the movable portion 3 and magnetically polarized in the directions orthogonal to the axis C, the voice coil motor 10 capable of relatively moving the movable portion 3 with respect to the fixed portion in the axis C direction is provided, and the two groups of magnets adjacent to each other in the circumferential direction in the cross section orthogonal to the axis C among a plurality of magnets 12 are arranged so as to be shifted in the opposite directions in the circumferential direction, so that the driving efficiency when the movable portion 3 is driven is improved and the voice coil motor 10 may be made compact. Therefore, it is possible to realize a smaller and lighter actuator that moves the movable lens forward and backward.

Also, according to the first embodiment, by forming the fixed portion 2 of the material having the relative magnetic permeability larger than 1.0, it is possible to generate the suction force between the same and the magnet 12, and to arrange the two groups of magnets adjacent to each other in the circumferential direction so as to be surely shifted in the opposite directions in the circumferential direction in a plane orthogonal to the axis C.

Also, according to the first embodiment, the fixed side sliding surface 24 of the fixed portion main body 20 is brought into contact with the movable side sliding surface 31c of the movable portion 3 also during operation of the movable portion 3, it is possible to inhibit the movable portion 3 from inclining with respect to the fixed portion 2 and to accurately move the movable portion 3.

Also, according to the first embodiment, by forming the fixed portion 2 of the fixed portion main body 20, the front frame portion 4, and the back frame portion 5, it is possible to decrease the number of parts and assembling steps and to increase a degree of freedom in design, thereby realizing a low cost.

Also, according to the first embodiment, since the coil 11 is wound around the axis C, a sliding axis of the movable portion 3 and an action axis of thrust generated by the voice coil motor 10 may be made the same, so that it becomes possible to drive with stability.

Also, according to the first embodiment, since the fixed side sliding surface 24 of the fixed portion 2 is formed so as to be divided in the circumferential direction, it is possible to make the optical unit 1 compact with a simple structure.

Also, according to the first embodiment, the magnet 12 includes a plurality of groups of the first magnet 12a and the second magnet 12b adjacent to each other in the axis C direction whose magnetic polarization directions are opposite to each other, a plurality of first magnets 12a has the same magnetic polarization direction, the coil 11 includes the first coil 11a opposed to a plurality of first magnets 12a and the second coil 11b opposed to a plurality of second magnets 12b to be connected to the first coil 11a, and the directions of the current flowing through the first coil 11a and the second coil 11b are opposite to each other, so that it is possible to increase the driving force.

Meanwhile, in the first embodiment, it is also possible to realize the arrangement of the magnets 12 similar to that illustrated in FIG. 2 by forming at least two step portions 31e adjacent to each other in the circumferential direction so as to be shifted in the opposite directions in the circumferential direction.

Variation 1-1

Figure 11:
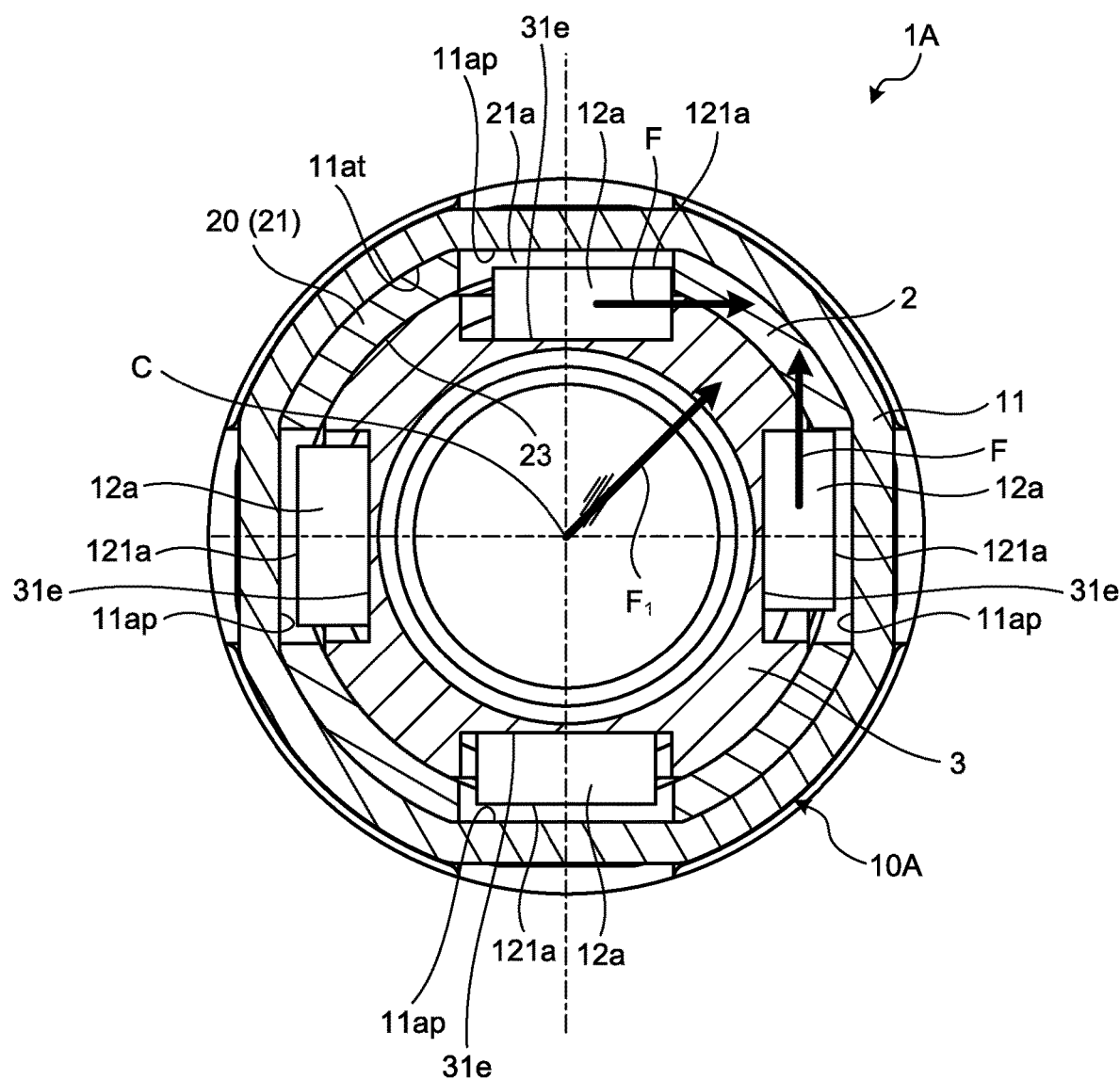
FIG. 11 is a cross-sectional view illustrating a configuration of an optical unit according to a variation 1-1 of the first embodiment.

FIG. 11 is a cross-sectional view illustrating a configuration of an optical unit according to a variation 1-1 of the first embodiment. An optical unit 1A illustrated in this drawing is provided with a fixed portion 2, a movable portion 3, and a voice coil motor 10A. The voice coil motor 10A is different from the voice coil motor 10 in arrangement of magnets 12 in the movable portion 3. In this variation 1-1, a portion having a configuration similar to that of the first embodiment is described by using the same reference sign as that in the first embodiment. This also applies to variations 1-2 to 1-4 described later.

As illustrated in FIG. 11, the magnet 12 includes four first magnets 12a and four second magnets 12b arranged side by side in an axis C direction so as to be opposed to planar portions 11ap and 11bp on an inner side of the planar portion 11ap of a first coil 11a and the planar portion 11bp of a second coil 11b, respectively. This variation 1-1 is different from the first embodiment in that the first magnets 12a arranged on a lower side and a left side of the axis C in FIG. 11 are evenly arranged without being shifted to one side in a circumferential direction of a step portion 31e. In this case, a direction of resultant force $F_1$ of suction forces F received by the first magnets 12a from the fixed portion 2 is a radial direction of the movable portion 3.

Meanwhile, the arrangement of the second magnets 12b in a cross section orthogonal to the axis C is similar to that of the first magnets 12a described above. Therefore, the direction of the resultant force of the suction forces received by the second magnets 12b from the fixed portion 2 is the same as the direction of the resultant force $F_1$ described above.

According to the variation 1-1 having the above-described configuration, in addition to an effect similar to that of the first embodiment, a backlash caused by sliding between the fixed portion 2 and the movable portion 3 may be gathered in one direction (direction of resultant force of suction forces) and tilt about an axis orthogonal to the axis C and shift in a direction parallel to the axis C of the movable portion 3 may be inhibited.

Variation 1-2

Figure 12:
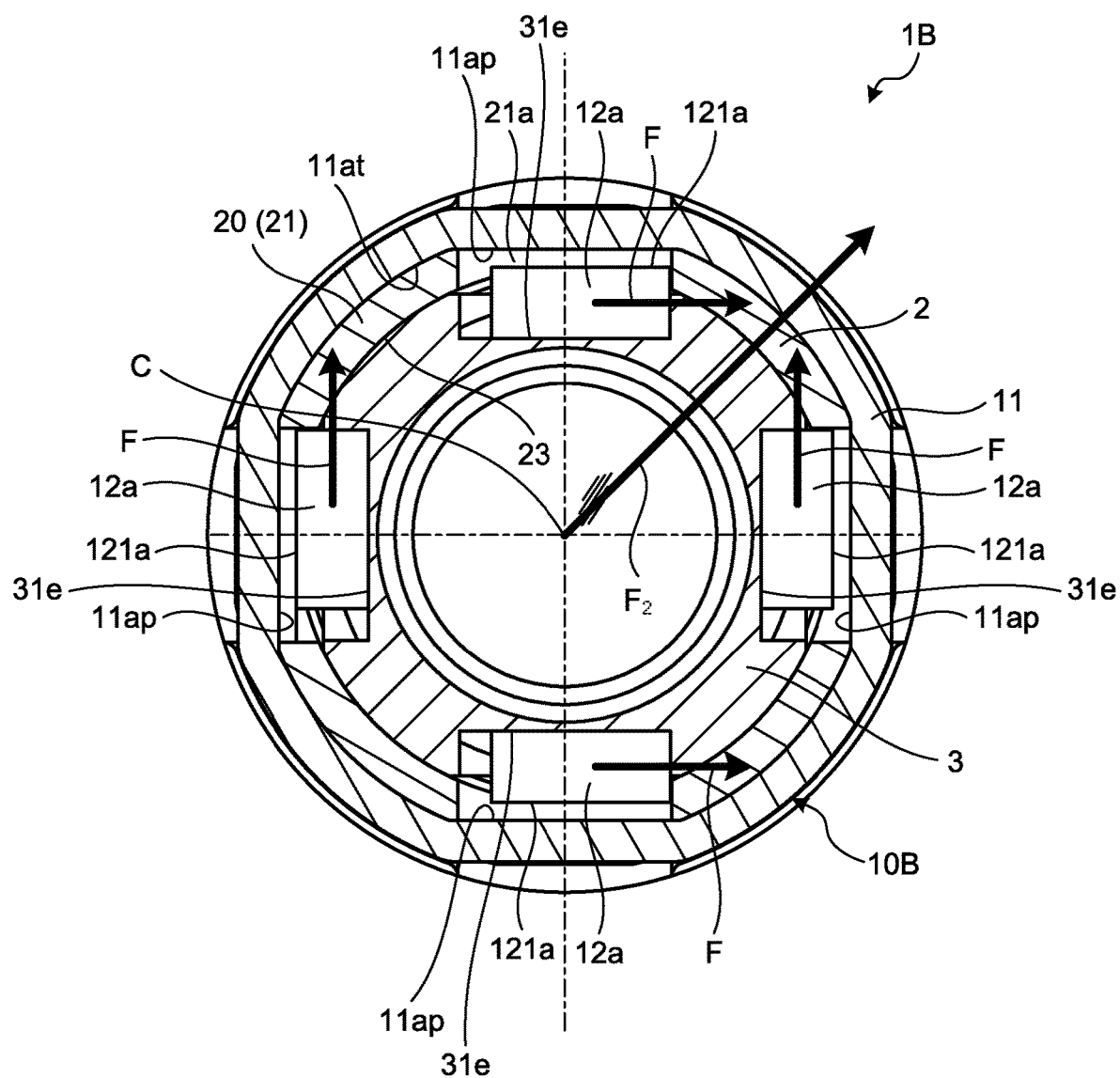
FIG. 12 is a cross-sectional view illustrating a configuration of an optical unit according to a variation 1-2 of the first embodiment.

FIG. 12 is a cross-sectional view illustrating a configuration of an optical unit according to a variation 1-2 of the first embodiment. An optical unit 1B illustrated in this drawing is provided with a fixed portion 2, a movable portion 3, and a voice coil motor 10B. The voice coil motor 10B is different from the voice coil motor 10 in arrangement of magnets 12 in the movable portion 3.

As illustrated in FIG. 12, the magnet 12 includes four first magnets 12a and four second magnets 12b arranged side by side in an axis C direction so as to be opposed to planar portions 11ap and 11bp on an inner side of the planar portion 11ap of a first coil 11a and the planar portion 11bp of a second coil 11b, respectively. The variation 1-2 is different from the first embodiment in that when the four first magnets 12a are seen in a cross section orthogonal to the axis C, the first magnets 12a arranged on a lower side and a left side of the axis C are arranged so as to be shifted in directions apart from each other in a circumferential direction. In this case, a direction of resultant force $F_2$ of suction forces F received by the first magnets 12a from the fixed portion 2 is a radial direction of the movable portion 3.

Meanwhile, the arrangement of the second magnets 12b in a cross section orthogonal to the axis C is similar to that of the first magnets 12a described above. Therefore, the direction of the resultant force of the suction forces received by the second magnets 12b from the fixed portion 2 is the same as the direction of the resultant force $F_2$ described above.

According to the variation 1-2 having the above-described configuration, in addition to an effect similar to that of the first embodiment, a backlash caused by sliding between the fixed portion 2 and the movable portion 3 may be gathered in one direction (direction of resultant force of suction forces) and tilt about an axis orthogonal to the axis C and shift in a direction parallel to the axis C of the movable portion 3 may be inhibited.

Variation 1-3

Figure 13:
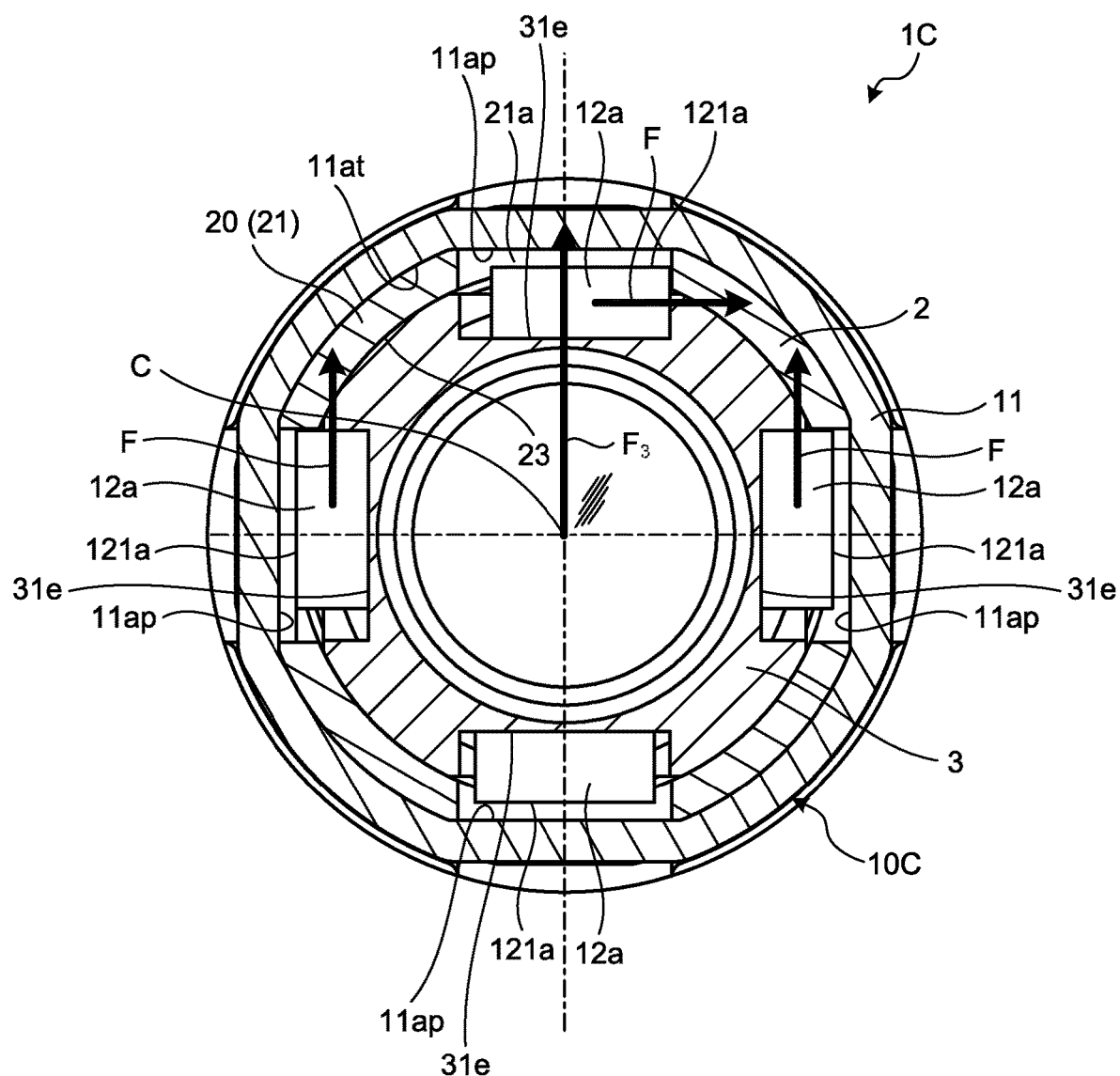
FIG. 13 is a cross-sectional view illustrating a configuration of an optical unit according to a variation 1-3 of the first embodiment.

FIG. 13 is a cross-sectional view illustrating a configuration of an optical unit according to variations 1-3 of the first embodiment. An optical unit 1C illustrated in this drawing is provided with a fixed portion 2, a movable portion 3, and a voice coil motor 10C. The voice coil motor 10C is different from the voice coil motor 10 in arrangement of magnets 12 in the movable portion 3.

As illustrated in FIG. 13, the magnet 12 includes four first magnets 12a and four second magnets 12b arranged side by side in an axis C direction so as to be opposed to planar portions 11ap and 11bp on an inner side the planar portion 11ap of a first coil 11a and the planar portion 11bp of a second coil 11b, respectively. This variation 1-3 is different from the first embodiment in a method of arranging the first magnets 12a located on a left side and a lower side of the axis C in FIG. 13. Specifically, when the four first magnets 12a are seen in a cross section orthogonal to the axis C, the first magnet 12a arranged on the left side of the axis C is arranged so as to be shifted in the same direction as the first magnet 12a arranged on an upper side of the axis C in a circumferential direction of the movable portion 3. Also, in FIG. 13, the first magnet 12a arranged on the lower side of the axis C is evenly arranged without being shifted to one side in the circumferential direction of a step portion 31e. In this case, a direction of resultant force $F_3$ of suction forces F received by the first magnets 12a from the fixed portion 2 is a radial direction of the movable portion 3.

Meanwhile, the arrangement of the second magnets 12b in a cross section orthogonal to the axis C is similar to that of the first magnets 12a described above. Therefore, the direction of the resultant force of the suction forces received by the second magnets 12b from the fixed portion 2 is the same as the direction of the resultant force $F_3$ described above.

According to the variation 1-3 having the above-described configuration, in addition to an effect similar to that of the first embodiment, a backlash caused by sliding between the fixed portion 2 and the movable portion 3 may be gathered in one direction (direction of resultant force of suction forces) and tilt about an axis orthogonal to the axis C and shift in a direction parallel to the axis C of the movable portion 3 may be inhibited.

Although moment in the circumferential direction is generated in this variation 1-3, since there is partial moment canceled out in the opposite direction, rotation of the movable portion 3 around the axis C may be inhibited.

Variation 1-4

Figure 14:
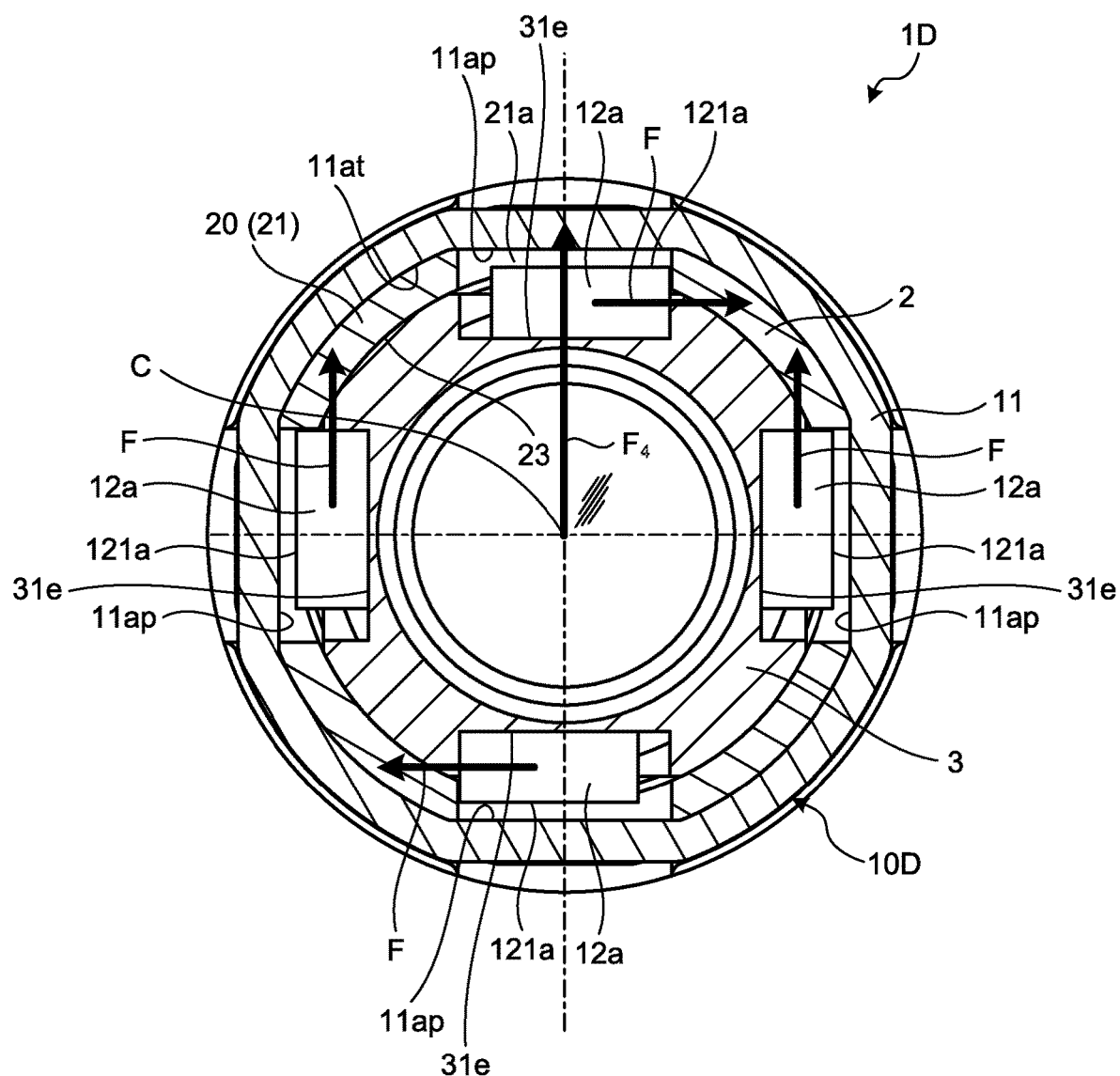
FIG. 14 is a cross-sectional view illustrating a configuration of an optical unit according to a variation 1-4 of the first embodiment.

FIG. 14 is a cross-sectional view illustrating a configuration of an optical unit according to a variation 1-4 of the first embodiment. An optical unit 1D illustrated in the drawing is provided with a fixed portion 2, a movable portion 3, and a voice coil motor 10D. The voice coil motor 10D is different from the voice coil motor 10 in arrangement of magnets 12 in the movable portion 3.

As illustrated in FIG. 14, the magnet 12 includes four first magnets 12a and four second magnets 12b arranged side by side in an axis C direction so as to be opposed to planar portions 11ap and 11bp on an inner side of the planar portion 11ap of a first coil 11a and the planar portion 11bp of a second coil 11b, respectively. The variation 1-4 is different from the first embodiment in that when the four first magnets 12a are seen in a cross section orthogonal to the axis C, the first magnet 12a arranged on a left side of the axis C is arranged so as to be shifted in the same direction as that of the first magnet 12a arranged on an upper side of the axis C in a circumferential direction of the movable portion 3. In this case, a direction of resultant force $F_4$ of suction forces F received by the first magnets 12a from the fixed portion 2 is a radial direction of the movable portion 3.

Meanwhile, the arrangement of the second magnets 12b in a cross section orthogonal to the axis C is similar to that of the first magnets 12a described above. Therefore, the direction of the resultant force of the suction forces received by the second magnets 12b from the fixed portion 2 is the same as the direction of the resultant force $F_4$ described above.

According to the variation 1-4 having the above-described configuration, in addition to an effect similar to that of the first embodiment, a backlash caused by sliding between the fixed portion 2 and the movable portion 3 may be gathered in one direction (direction of resultant force of suction forces) and tilt about an axis orthogonal to the axis C and shift in a direction parallel to the axis C of the movable portion 3 may be inhibited.

Although moment in the circumferential direction is generated in this variation 1-4, since there is partial moment canceled out in the opposite direction, rotation of the movable portion 3 around the axis C may be inhibited.

Second Embodiment

Figure 15:
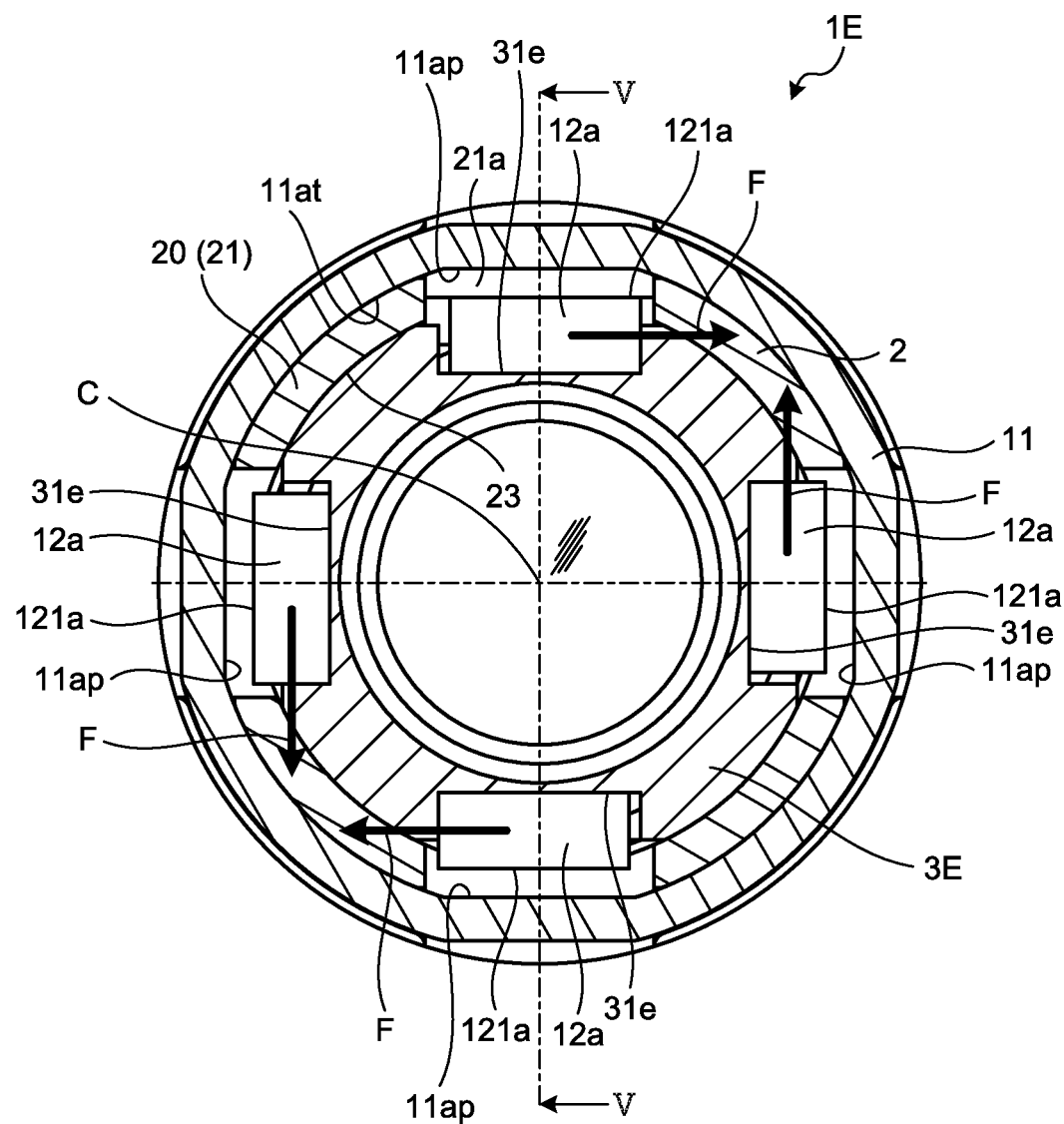
FIG. 15 is a cross-sectional view (part 1) illustrating a configuration of a substantial part of an optical unit according to a second embodiment.
Figure 16:
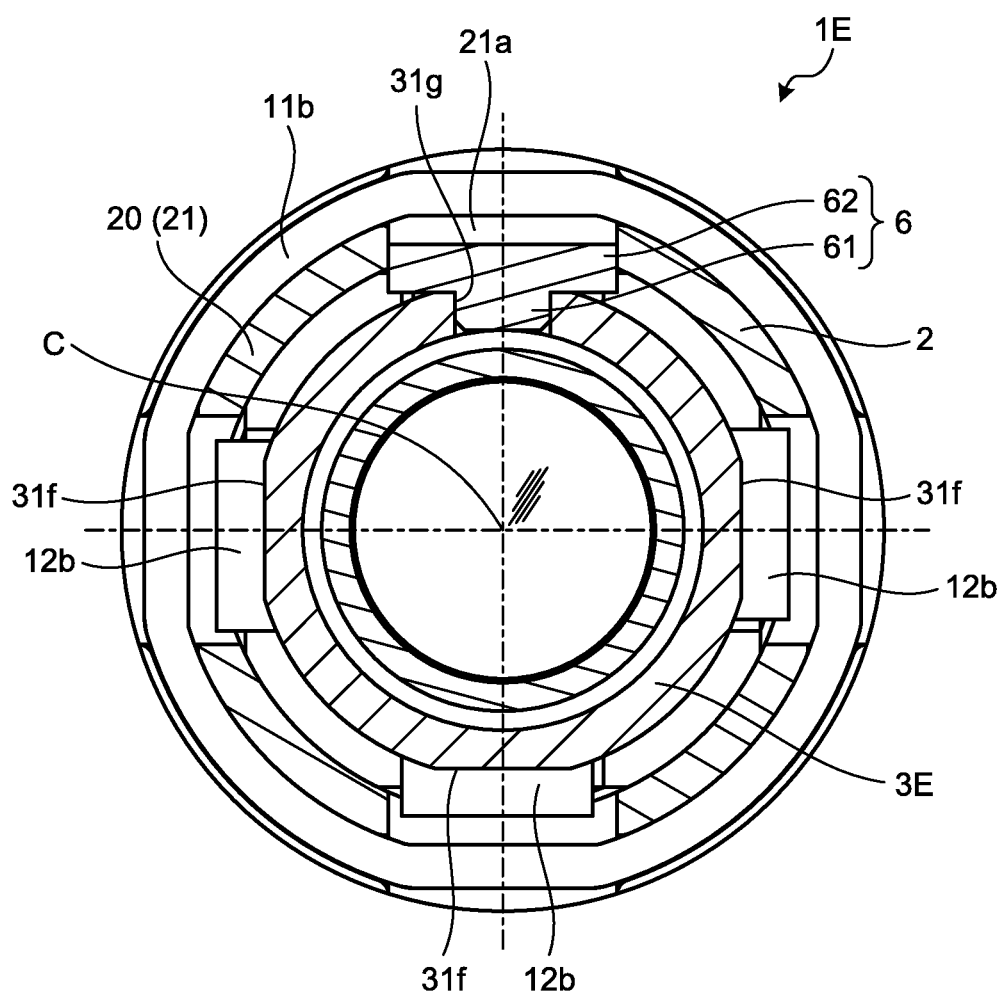
FIG. 16 is a cross-sectional view (part 2) illustrating the configuration of the substantial part of the optical unit according to the second embodiment.
Figure 17:
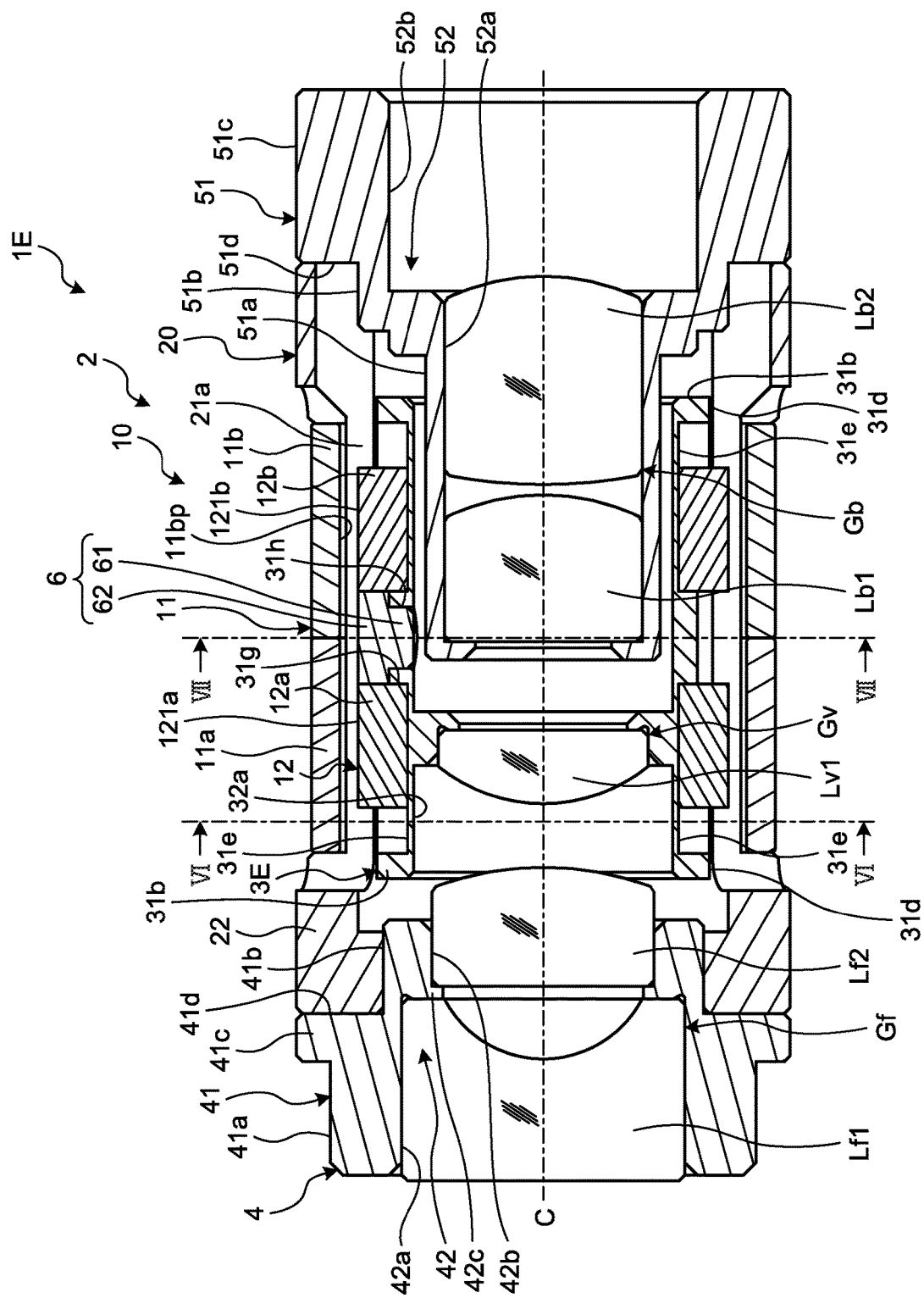
FIG. 17 is a cross-sectional view of the optical unit as seen in a cross section taken along line V-V of FIG. 15.

FIGS. 15 and 16 are cross-sectional views illustrating a configuration of a substantial part of an optical unit according to a second embodiment. FIG. 17 is a cross-sectional view of the optical unit as seen in a cross section taken along line V-V of FIG. 15. Meanwhile, FIG. 15 also is a cross-sectional view as seen in a cross section taken along line VI-VI of FIG. 17. FIG. 16 also is a cross-sectional view as seen in a cross section taken along line VII-VII of FIG. 17. An optical unit 1E illustrated in FIGS. 15 to 17 is provided with a fixed portion 2, a movable portion 3E, a voice coil motor 10, and a rotation regulating unit 6 mounted on the movable portion 3E. In the second embodiment, a portion having a configuration similar to that of the first embodiment is described by using the same reference sign as that in the first embodiment.

Figure 18:
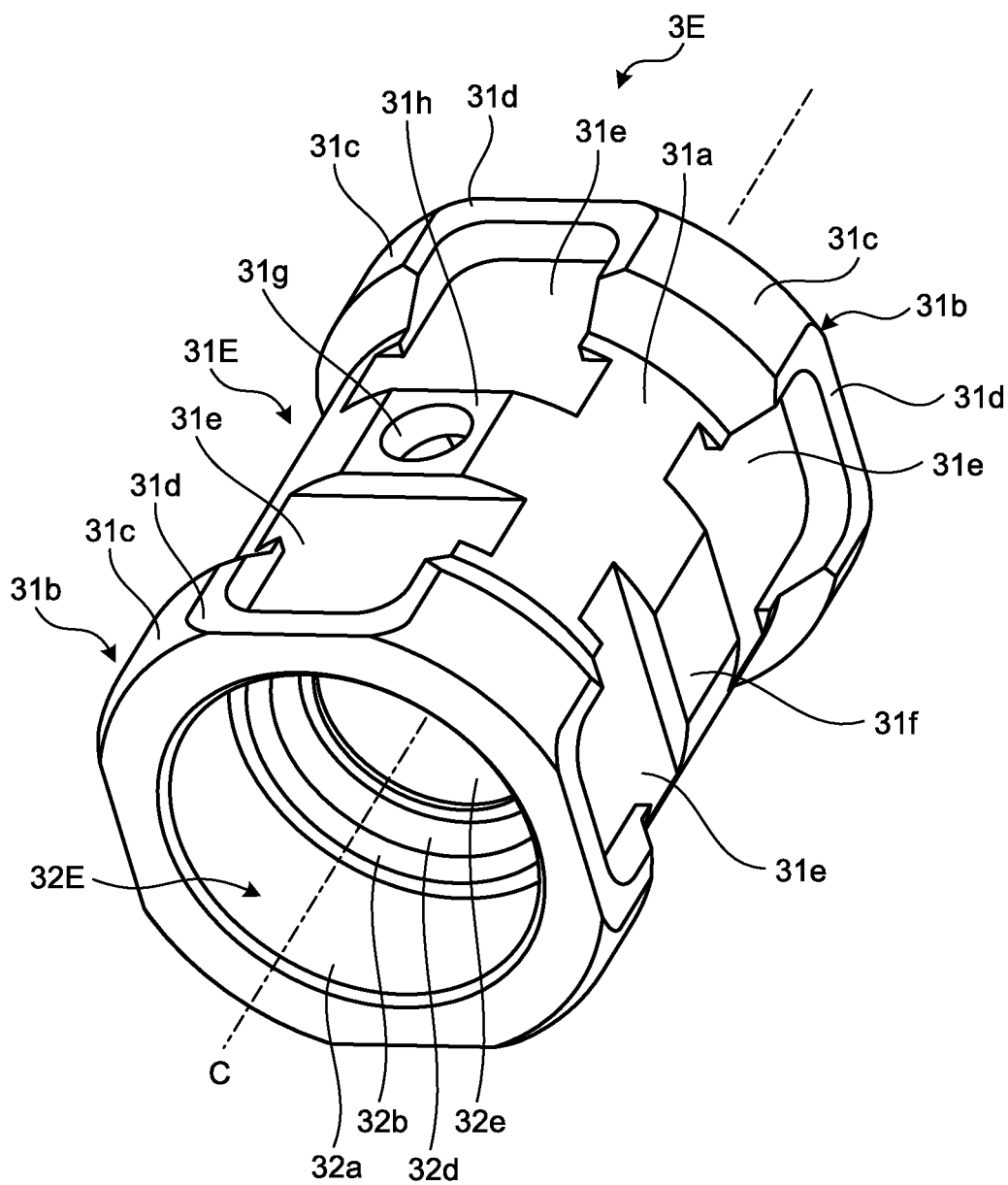
FIG. 18 is a perspective view illustrating a configuration of a movable portion of the optical unit according to the second embodiment.

FIG. 18 is a perspective view illustrating a configuration of the movable portion 3E. As illustrated in FIG. 18, the movable portion 3E is formed of a tubular member having an outer peripheral portion 31E and an inner peripheral portion 32E.

The outer peripheral portion 31E includes a tubular portion 31a and a projecting edge portion 31b. The projecting edge portion 31b includes a movable side sliding surface 31c and a planar portion 31d.

In a case illustrated in FIG. 18, the projecting edge portion 31b includes four movable side sliding surfaces 31c and four planar portions 31d alternately in a circumferential direction around an axis C at a regular interval. The planar portion 31d passes through the same plane as any of the four planar portions 31d formed on the other end side in the axis C direction. In other words, the outer peripheral portion 31E includes four groups of the two planar portions 31d formed on different end portions and passing through the same plane. A step portion 31e is provided between each of the four groups of the planar portions 31d. At the center in the axis C direction of the step portion 31e provided between each of the three groups of the planar portions 31d out of the four groups of the planar portions 31*d*, a cutout portion 31*f* having a planar outer periphery obtained by cutting out a surface of the tubular portion 31*a* is provided.

At the center in the axis C direction of the step portion 31*e* formed between one remaining group of the planar portions 31*d* out of the four groups of the planar portions 31*d*, a holding unit 31*h* that holds the rotation regulating unit 6 is provided by forming a hole portion 31*g* penetrating in a radial direction on a portion having the planar outer periphery obtained by cutting out the surface of the tubular portion 31*a*. Meanwhile, the hole portion 31*g* may also have a shape with a bottom on an inner peripheral side in the radial direction of the outer peripheral portion 31E.

The inner peripheral portion 32E of the movable portion 3E includes a first inner peripheral portion 32*a*, a second inner peripheral portion 32*b*, a third inner peripheral portion 32*e*, and an inner peripheral side convex portion 32*d*. An aperture of the hole portion 31*g* is formed on the third inner peripheral portion 32*e*.

Figure 19:
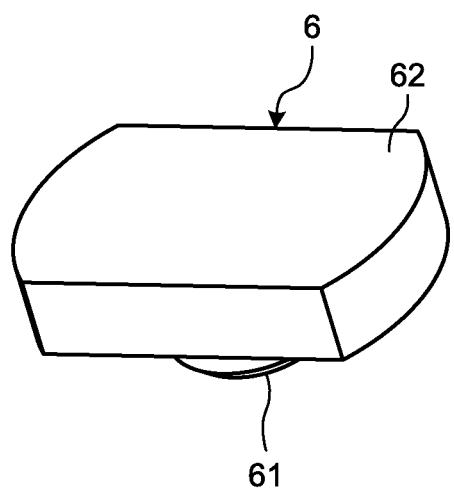
FIG. 19 is a perspective view illustrating a configuration of a rotation regulating unit of the optical unit according to the second embodiment.

FIG. 19 is a perspective view illustrating a configuration of the rotation regulating unit 6. The rotation regulating unit 6 includes a cylindrical insertion portion 61 having a diameter that allows insertion into the hole portion 31*g* of the movable portion 3E and a head portion 62 provided on one end in a height direction of the insertion portion 61 which is mounted on an outer peripheral side surface of the holding unit 31*h* and projects from the holding unit 31*h* toward an outer periphery in the radial direction in a state in which the insertion portion 61 is inserted into the hole portion 31*g*. A portion of a side surface of the head portion 62 which is in contact with the fixed portion 2 has a curved R shape while the side surface opposed to a first magnet 12*a* and a second magnet 12*b* is planar. The rotation regulating unit 6 is fixed to the movable portion 3E by adhesion and the like in a state of being held by the holding unit 31*h*. Meanwhile, a surface shape of the rotation regulating unit parallel to the axis C in a state of being fixed to the movable portion 3E may be a circular shape or a rectangular shape.

As illustrated in FIG. 16, a width in the circumferential direction in a plane orthogonal to the axis C of the head portion 62 of the rotation regulating unit 6 is larger than a width in the circumferential direction of the magnet 12 (second magnet 12*b* is illustrated in FIG. 16) in the same plane.

According to the second embodiment described above, it is possible to obtain an effect similar to that of the above-described first embodiment.

Also, according to the second embodiment, the movable portion 3E and the rotation regulating unit 6 are separated from each other, so that the movable portion 3E and the rotation regulating unit 6 may be processed more easily.

Meanwhile, although the rotation regulating unit 6 is formed separately from the movable portion 3E in the second embodiment, the movable portion and the rotation regulating unit may also be integrally formed.

Also, a plurality of rotation regulating units 6 may be provided. Meanwhile, in order to provide an economical optical unit while decreasing a manufacturing cost without unnecessarily raising requirement accuracy for parts in addition to realizing downsizing and light weight, it is more preferable that the number of the rotation regulating units 6 be as small as possible.

Third Embodiment

Figure 20:
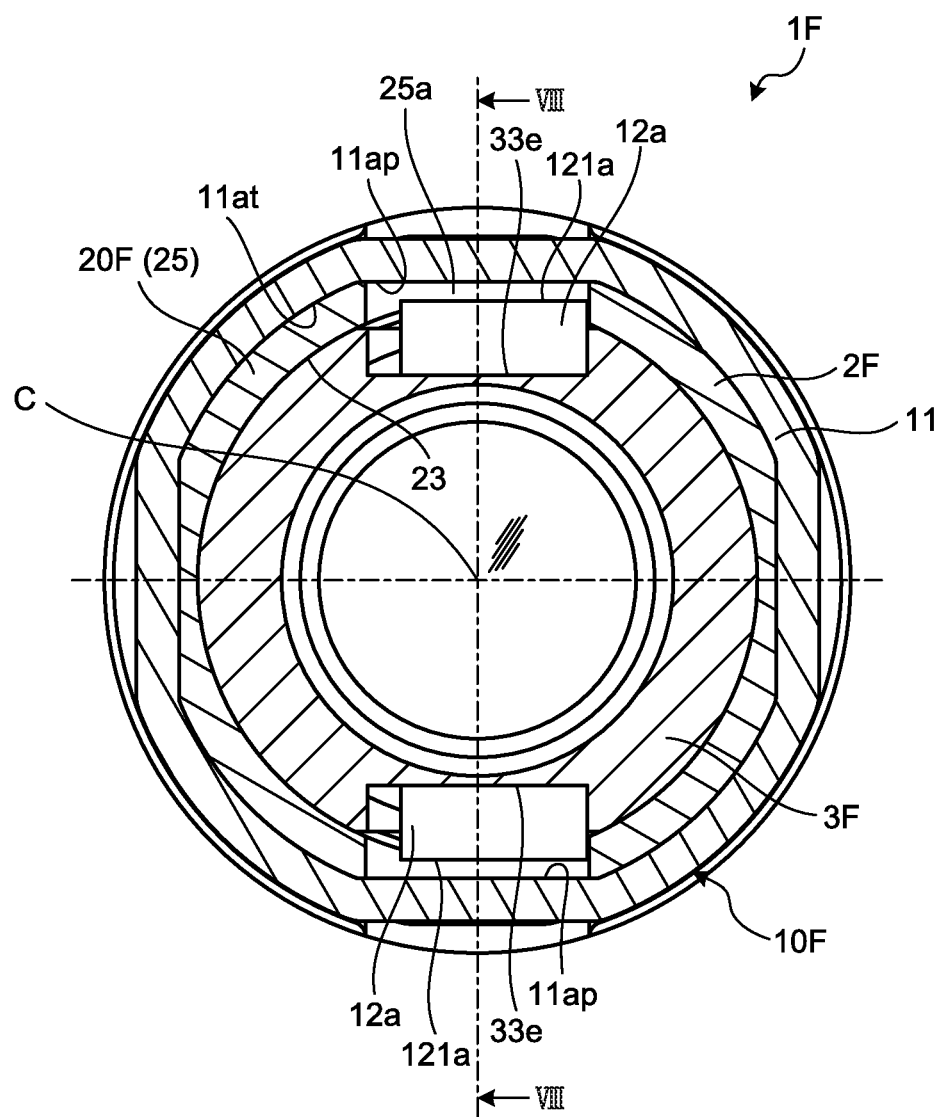
FIG. 20 is a cross-sectional view illustrating a configuration of a substantial part of an optical unit according to a third embodiment.
Figure 21:
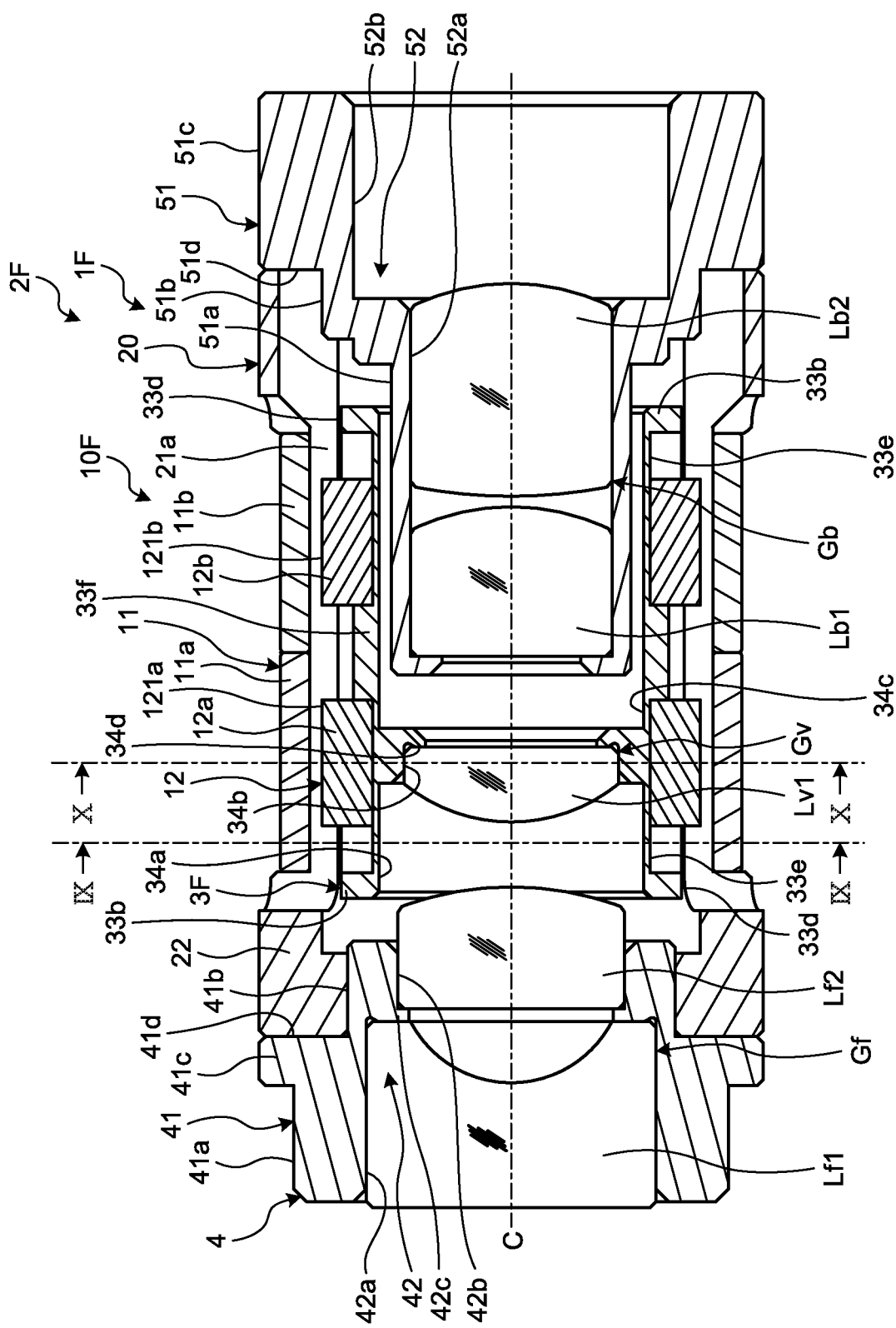
FIG. 21 is a cross-sectional view of the optical unit as seen in a cross section taken along line VIII-VIII of FIG. 20.

FIG. 20 is a cross-sectional view illustrating a configuration of a substantial part of an optical unit according to a third embodiment. FIG. 21 is a cross-sectional view of the optical unit as seen in a cross section taken along line VIII-VIII in FIG. 20. Meanwhile, FIG. 20 also is a cross-sectional view of the optical unit as seen in a cross section taken along line IX-IX of FIG. 21.

An optical unit 1F illustrated in FIGS. 20 and 21 is provided with a fixed portion 2F, a movable portion 3F, and a voice coil motor 10F. The voice coil motor 10F is different from the voice coil motor 10 at least in the number of magnets 12. In the third embodiment, a portion having a configuration similar to that of the first embodiment is described by using the same reference sign as that in the first embodiment.

Figure 22:
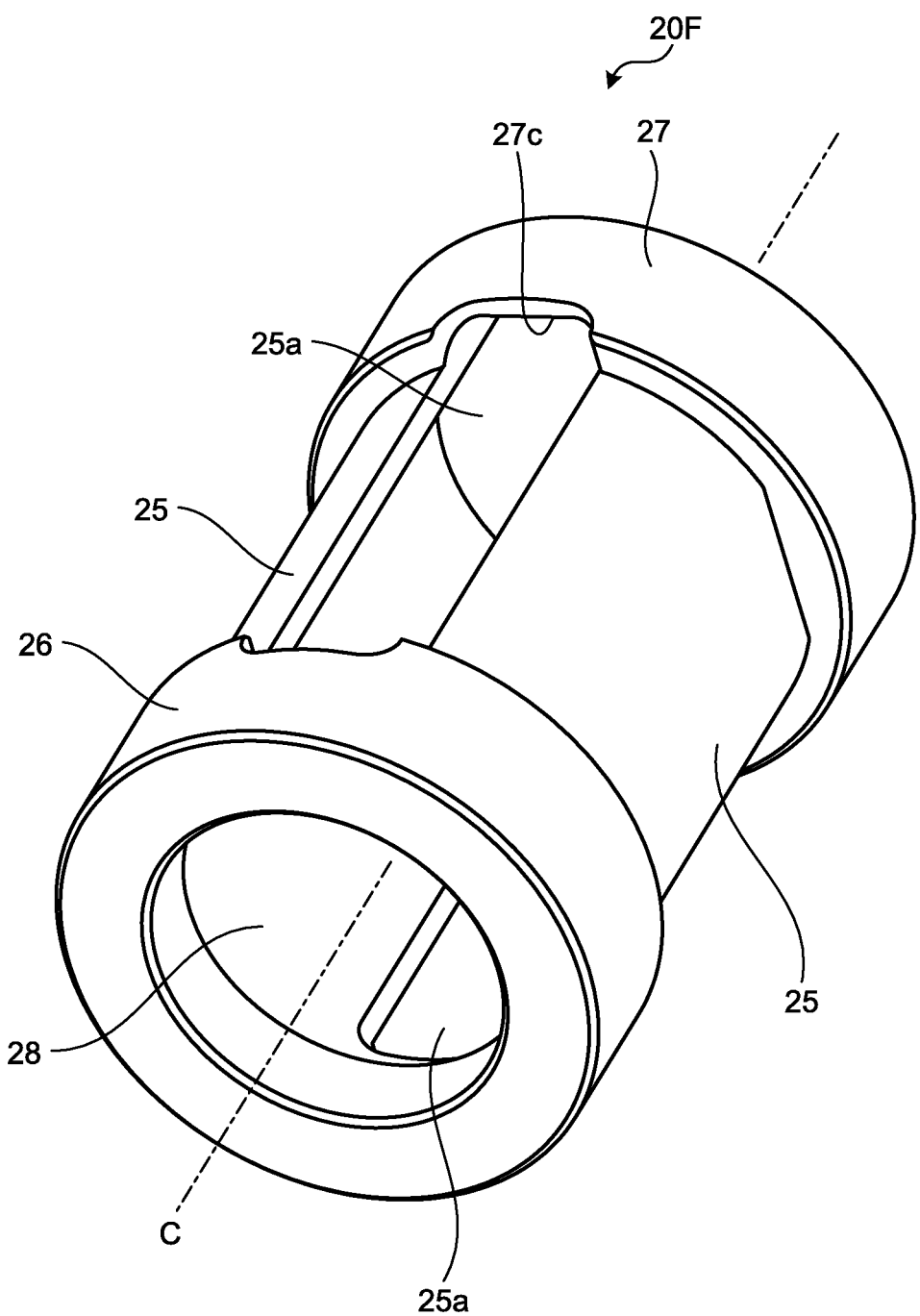
FIG. 22 is a perspective view illustrating a configuration of a fixed portion main body of the optical unit according to the third embodiment.

FIG. 22 is a perspective view illustrating a configuration of a fixed portion main body 20F included in the fixed portion 2F. The fixed portion main body 20F illustrated in this drawing is formed of a tubular member centered around a predetermined axis C. The fixed portion main body 20F includes a tubular portion 25 having the axis C as a central axis, an object side thick portion 26 formed on an object side in an axis C direction with respect to the tubular portion 25, and an image side thick portion 27 formed on an image side in the axis C direction with respect to the tubular portion 25.

Two first thinned portions 25*a* are formed in the tubular portion 25. Specifically, the two first thinned portions 25*a* are formed in positions 180-degree rotational symmetrical with respect to the axis C. A radially inner surface of the tubular portion 25 except the first thinned portions 25*a* is a tubular cylindrical surface and serves as a fixed side sliding surface 28 for guiding and supporting the movable portion 3F. The fixed side sliding surface 28 has a shape divided in a circumferential direction by the first thinned portions 25*a*.

The object side thick portion 26 is formed to project radially outward and radially inward from the tubular portion 25. The image side thick portion 27 is formed so as to project radially outward from the tubular portion 25. A groove 27*c* through which the magnet 12 passes when the movable portion 3F is assembled is formed on the fixed side sliding surface 28 on a radially inner side of the image side thick portion 27. Therefore, it becomes possible to smoothly assemble the movable portion 3F with respect to the fixed portion main body 20F. Meanwhile, a structure may be such that the object side thick portion 26 and the image side thick portion 27 are formed separately from the tubular portion 25 to be attached to the tubular portion 25 at the time of assembly.

Figure 23:
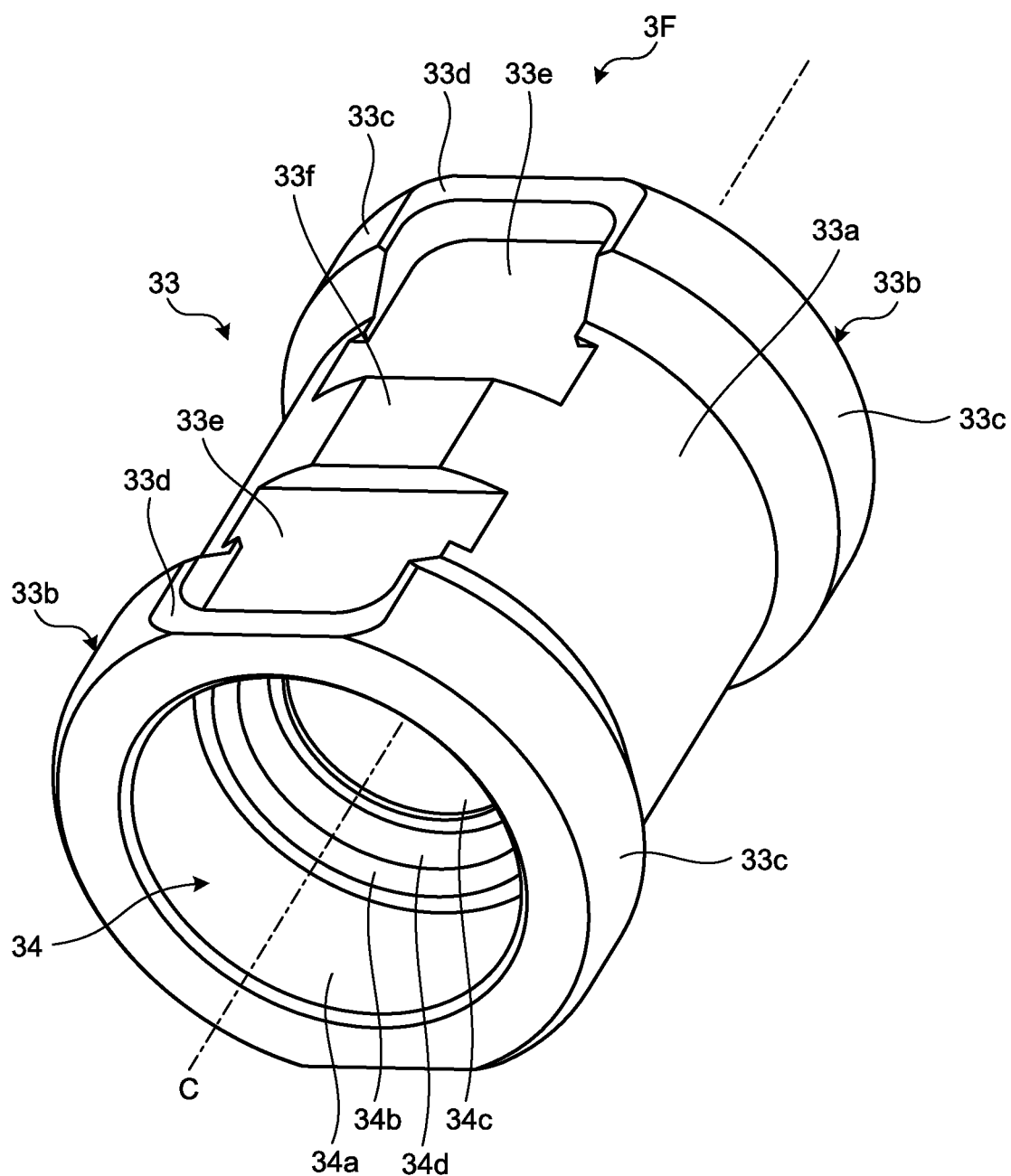
FIG. 23 is a perspective view illustrating a configuration of a movable portion of the optical unit according to the third embodiment.

FIG. 23 is a perspective view illustrating a configuration of the movable portion 3F. The movable portion 3F illustrated in this drawing is formed of a tubular member including an outer peripheral portion 33 and an inner peripheral portion 34.

The outer peripheral portion 33 includes a tubular portion 33*a* and two projecting edge portions 33*b* formed on both end portions in the axis C direction of the tubular portion 33*a* each having a larger outer peripheral diameter than that of the tubular portion 33*a*. The tubular portion 33*a* and the projecting edge portion 33*b* may be formed as an integral member or as separate members.

The projecting edge portion 33*b* includes a movable side sliding surface 33*c* formed of an outer peripheral surface thereof and a planar portion 33*d* formed on a part of a radially outer side of the projecting edge portion 33*b*. In a case illustrated in FIG. 23, the projecting edge portion 33*b* includes two movable side sliding surfaces 33*c* and two planar portions 33*d* alternately in a circumferential direction around the axis C. The planar portion 33*d* passes through the same plane as any of the two planar portions 33*d* formed on the other end side in the axis C direction. In other words, the outer peripheral portion 33 includes two groups of the two planar portions 33d formed on different end portions and passing through the same plane.

A step portion 33e formed radially inside the tubular portion 33a including a planar outer peripheral surface is provided between each of the two groups of the planar portions 33d. At the center in the axis C direction of the step portion 33e, a cutout portion 33f having a planar outer periphery obtained by cutting out a surface of the tubular portion 33a is provided.

The inner peripheral portion 34 includes a first inner peripheral portion 34a, a second inner peripheral portion 34b, a third inner peripheral portion 34c, and an inner peripheral side convex portion 34d. The second inner peripheral portion 34b is smaller in diameter than the first inner peripheral portion 34a and the third inner peripheral portion 34c. The inner peripheral side convex portion 34d having the smallest diameter projecting radially inward is provided between the second inner peripheral portion 34b and the third inner peripheral portion 34c. The second inner peripheral portion 34b holds a movable first lens Lv1 included in a movable lens group Gv. As illustrated in FIG. 21, the image side of the movable first lens Lv1 preferably abuts the inner peripheral side convex portion 34d.

The movable portion 3F is inserted into the fixed portion main body 20F while the movable side sliding surface 33c is in contact with the fixed side sliding surface 28. Also, as illustrated in FIG. 21, the former is inserted into the latter such that a first outer peripheral portion 51a of a back frame portion 5 is opposed to a radially inner side of a third inner peripheral portion 34c of the movable portion 3F. According to this, at least a part of an image side fixed lens group Gb is located on the radially inner side of the third inner peripheral portion 34c of the movable portion 3F. When the movable portion 3F moves so as to be the closest to the object, at least a part of an object side fixed lens group Gf is located on the radially inner side of the first inner peripheral portion 34a of the movable portion 3F.

The voice coil motor 10F includes two groups in each of which a first magnet 12a and a second magnet 12b are arranged in this order along the axis C. When seen in a plane illustrated in FIG. 20, that is, the plane orthogonal to the axis C, the same type of magnets (first magnets 12a in FIG. 20) are provided in two positions at 180-degree interval in the circumferential direction.

Figure 24:
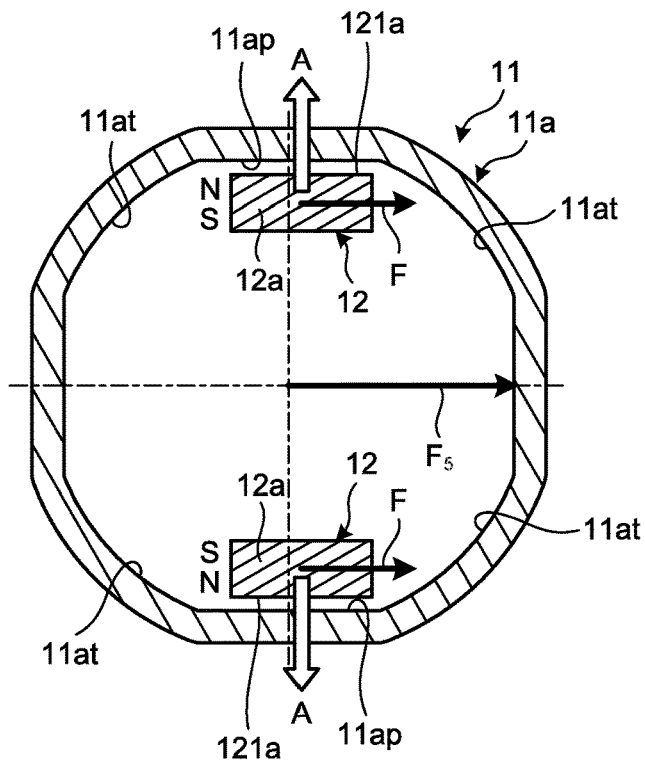
FIG. 24 is a cross-sectional view illustrating a configuration of only a voice coil motor as seen in a cross section taken along line X-X of FIG. 21.

FIG. 24 is a cross-sectional view illustrating a configuration of only a voice coil motor as seen in a cross section taken along line X-X of FIG. 21. In FIG. 24, black arrow F indicates suction force received by each first magnet 12a from the fixed portion 2F. In this case, resultant force of the suction forces received by the two first magnets 12a is substantially zero. The same applies to the two second magnets 12b.

Therefore, according to the third embodiment, rotational moment around the axis C becomes substantially zero, and frictional force between the fixed portion 2F and the movable portion 3F may be reduced. As a result, since driving efficiency when the movable portion 3F is driven is improved, and the voice coil motor 10F may be made compact.

Also, according to the third embodiment, the two magnets 12 are arranged so as to be shifted in a direction to approach the fixed portion 2F in the circumferential direction in a cross section orthogonal to the axis C, and a direction of resultant force $F_5$ of the suction forces received by the magnets 12 from the fixed portion 2F is set to a radial direction of the movable portion 3F, so that a backlash caused by sliding between the fixed portion 2F and the movable portion 3F may be gathered in one direction and tilt about an axis orthogonal to the axis C and shift in a direction parallel to the axis C of the movable portion 3F may be inhibited.

Figure 25:
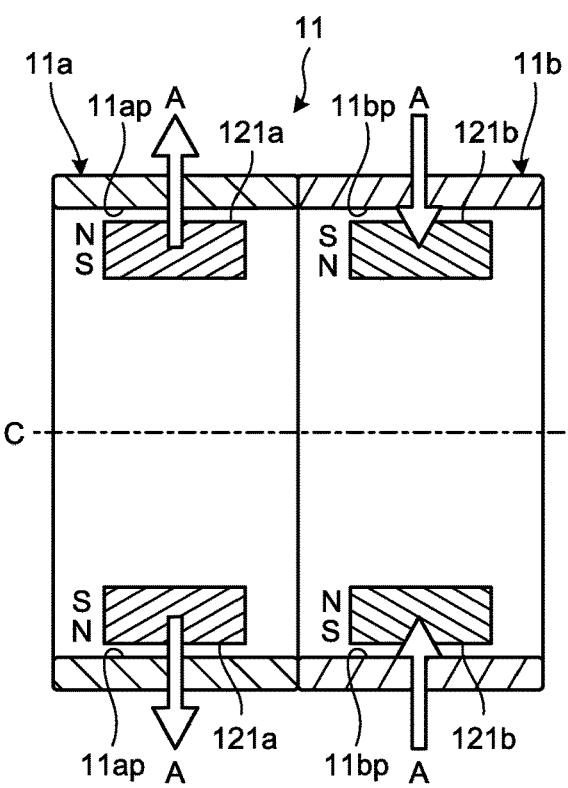
FIG. 25 is a view illustrating only the voice coil motor in the same cross section as FIG. 21.

FIG. 25 is a view illustrating only the voice coil motor in the same cross section as FIG. 21. As illustrated in FIGS. 24 and 25, the first magnet 12a and the second magnet 12b forming a group in the axis C direction are arranged apart from each other. A group of the first magnets 12a and a group of the second magnets 12b are magnetized in the radial direction with magnetic poles opposite to each other. In the case illustrated in FIGS. 24 and 25, the first magnet 12a has an N pole on a side of a first coil 11a and an S pole on the opposite side thereof, and the second magnet 12b has an S pole on a side of a second coil 11b and an N pole on the opposite side thereof. In this case, magnetic polarization directions of the first magnet 12a and the second magnet 12b are orthogonal to the axis C as indicated by outline arrows A in FIGS. 24 and 25. Meanwhile, in this third embodiment also, in more general, magnetic polarization direction of the first magnet 12a and the second magnet 12b may be the directions intersecting with the axis C.

According to the third embodiment described above, it is possible to obtain an effect similar to that of the above-described first embodiment.

Also, according to the third embodiment, the two magnets 12 arranged on the movable portion 3F are arranged so as to be shifted in the direction to approach the fixed portion 2F in the circumferential direction in a cross section orthogonal to the axis C, and the direction of the resultant force of the suction forces received by the magnets 12 from the fixed portion 2F is set to the radial direction of the movable portion 3F, so that the backlash caused by the sliding between the fixed portion 2F and the movable portion 3F may be gathered in one direction and tilt about the axis orthogonal to the axis C and shift in the direction parallel to the axis C of the movable portion 3F may be inhibited.

Also, according to the third embodiment, since the number of magnets 12 is reduced, it is possible to further reduce the size and weight.

Fourth Embodiment

Figure 26:
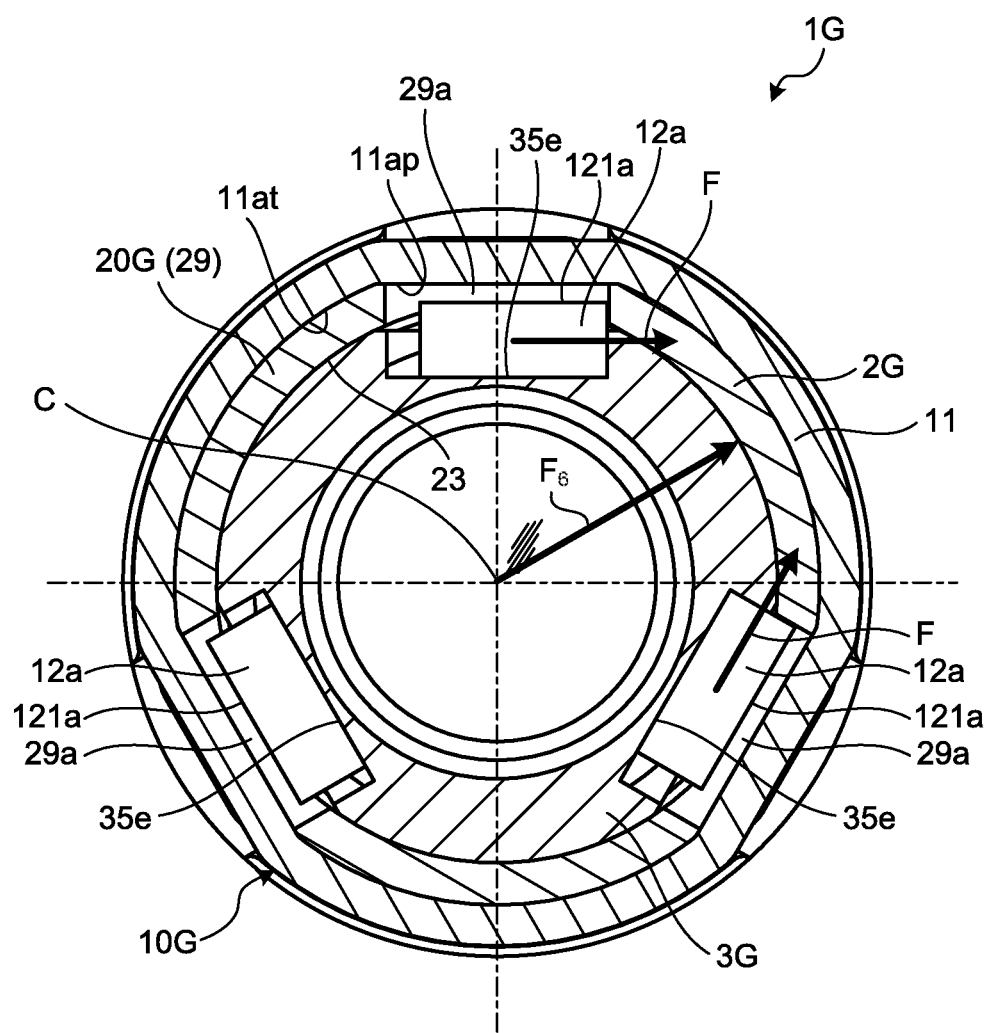
FIG. 26 is a cross-sectional view illustrating a configuration of an optical unit according to a fourth embodiment.

FIG. 26 is a cross-sectional view illustrating a configuration of an optical unit according to a fourth embodiment. An optical unit 1G illustrated in this drawing is provided with a fixed portion 2G, a movable portion 3G, and a voice coil motor 10G. The voice coil motor 10G is different from the voice coil motor 10 at least in the number of magnets 12. In the fourth embodiment, a portion having a configuration similar to that of the first embodiment is described by using the same reference sign as that in the first embodiment.

The magnet 12 includes three first magnets 12a and three second magnets 12b arranged side by side in an axis C direction so as to be opposed to planar portions 11ap and 11bp on an inner side of the planar portion 11ap of a first coil 11a and the planar portion 11bp of a second coil 11b, respectively.

Three thinned portions 29a are formed in a tubular portion 29 of a fixed portion main body 20G of the fixed portion 2G. Specifically, the three thinned portions 29a penetrating in a radial direction of the tubular portion 29 are formed at 120-degree interval with respect to the axis C being a central axis in a longitudinal direction of the tubular portion 29 (direction orthogonal to a plane of paper of FIG. 26).

The movable portion 3G on which the magnet 12 is arranged having a tubular shape is different from the movable portion 3 illustrated in FIG. 8 in the number of step portions and cutouts formed on the tubular portion 29. That is, three step portions 35e and three cutouts (not illustrated) are formed on the movable portion 3G. The movable portion 3G has 120-degree rotational symmetry in a cross section orthogonal to the axis C being the central axis. Therefore, when the optical unit 1G is assembled, the three magnets 12 are inserted into the three thinned portions 29a formed on the fixed portion main body 20G, respectively.

When the three first magnets 12a are seen in the cross section orthogonal to the axis C, intervals between the adjacent first magnets 12a in a circumferential direction around the axis C are not equal, and there is one group with a smaller interval. Specifically, the interval in the circumferential direction between the first magnet 12a located on an upper side of the axis C and the first magnet 12a located on a lower right side in FIG. 26 is the smallest. Also, in FIG. 26, the first magnet 12a located on a lower left side of the axis C is evenly arranged without being shifted to one side in the circumferential direction of the step portion 35e.

In the fourth embodiment having such a configuration, a direction of resultant force $F_6$ of suction forces F received by the two first magnets 12a having the smallest interval in the circumferential direction in FIG. 26 from the movable portion 3G is a radial direction of the movable portion 3G. Meanwhile, although the arrangement of the first magnets 12a is illustrated in FIG. 26, the arrangement of the second magnets 12b is similar to this. Therefore, the direction of the resultant force $F_6$ received by the second magnets 12b from the movable portion 3G is also the radial direction of the movable portion 3G. Therefore, it is possible to gather a backlash caused by sliding between the fixed portion 2G and the movable portion 3G in one direction and inhibit tilt around an axis orthogonal to the axis C and shift in a direction parallel to the axis C of the movable portion 3G.

According to the fourth embodiment described above, it is possible to obtain an effect similar to that of the above-described first embodiment.

Also, according to the fourth embodiment, the two adjacent magnets 12 out of the magnets 12 arranged on the movable portion 3G are arranged so as to be shifted in a direction to approach the fixed portion 2G in the circumferential direction, and the direction of the resultant force of the suction forces received by the magnets 12 from the fixed portion 2G is set to the radial direction of the movable portion 3G, so that the backlash caused by the sliding between the fixed portion 2G and the movable portion 3G may be gathered in one direction and tilt about the axis orthogonal to the axis C and shift in the direction parallel to the axis C of the movable portion 3G may be inhibited.

Variation 4-1

Figure 27:
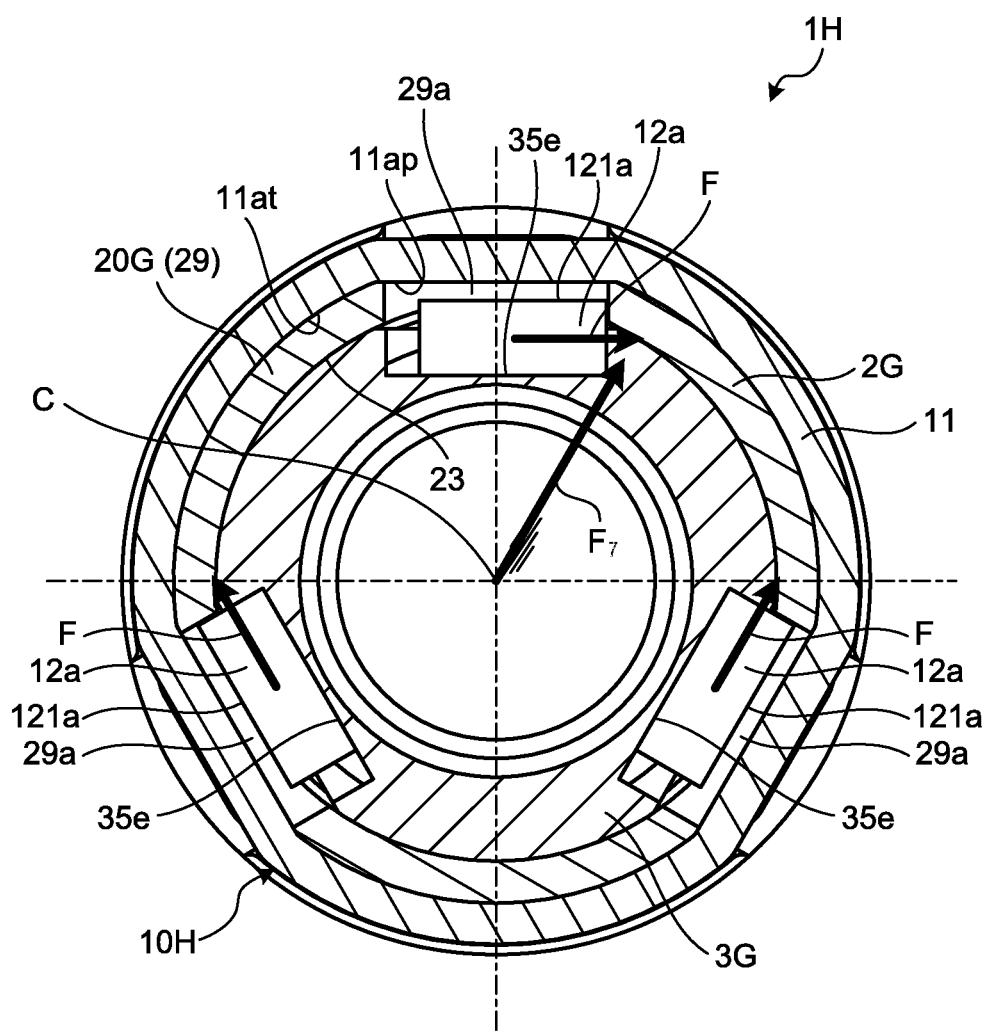
FIG. 27 is a cross-sectional view illustrating a configuration of an optical unit according to a variation 4-1 of the fourth embodiment.

FIG. 27 is a cross-sectional view illustrating a configuration of an optical unit according to a variation 4-1 of the fourth embodiment. An optical unit 1H illustrated in this drawing is provided with a fixed portion 2G, a movable portion 3G, and a voice coil motor 10H. The voice coil motor 10H is different from the voice coil motor 10G in the number of magnets 12 and arrangement in the movable portion 3G. In this variation 4-1, a portion having a configuration similar to that of the fourth embodiment is described by using the same reference sign as that in the fourth embodiment.

The magnet 12 includes three first magnets 12a and three second magnets 12b arranged side by side in an axis C direction so as to be opposed to planar portions 11ap and 11bp on an inner side of the planar portion 11ap of a first coil 11a and the planar portion 11bp of a second coil 11b, respectively. In the variation 4-1, out of the three first magnets 12a located on an upper side, a lower right side, and a lower left side of the axis C in FIG. 27, an interval in a circumferential direction between the first magnet 12a located on the upper side and the first magnet 12a located on the lower right side is the smallest. Also, in FIG. 27, the first magnet 12a located on the lower left side of the axis C is arranged so as to be shifted in a direction approaching the first magnet 12a located on the upper side of the axis C in the circumferential direction of the movable portion 3G. Therefore, in FIG. 27, the first magnet 12a located on the lower left side of the axis C receives suction force in the same direction as the first magnet 12a located on the upper side of the axis C in the circumferential direction of the movable portion 3G.

By arranging in this manner, a direction of resultant force $F_7$ of the suction forces F received by the three first magnets 12a from the movable portion 3G is a radial direction of the movable portion 3G. Meanwhile, although the arrangement of the first magnets 12a is illustrated in FIG. 27, since the arrangement of the second magnets 12b is similar to the same, the direction of the resultant force $F_7$ received by the second magnets 12b from the movable portion 3G is also the radial direction of the movable portion 3G. Therefore, it is possible to gather a backlash caused by sliding between the fixed portion 2G and the movable portion 3G in one direction and inhibit tilt around an axis orthogonal to the axis C and shift in a direction parallel to the axis C of the movable portion 3G.

Although moment in the circumferential direction is generated in this variation 4-1, since there is partial moment in the opposite direction, rotation of the movable portion 3G around the axis C may be inhibited.

Fifth Embodiment

Figure 28:
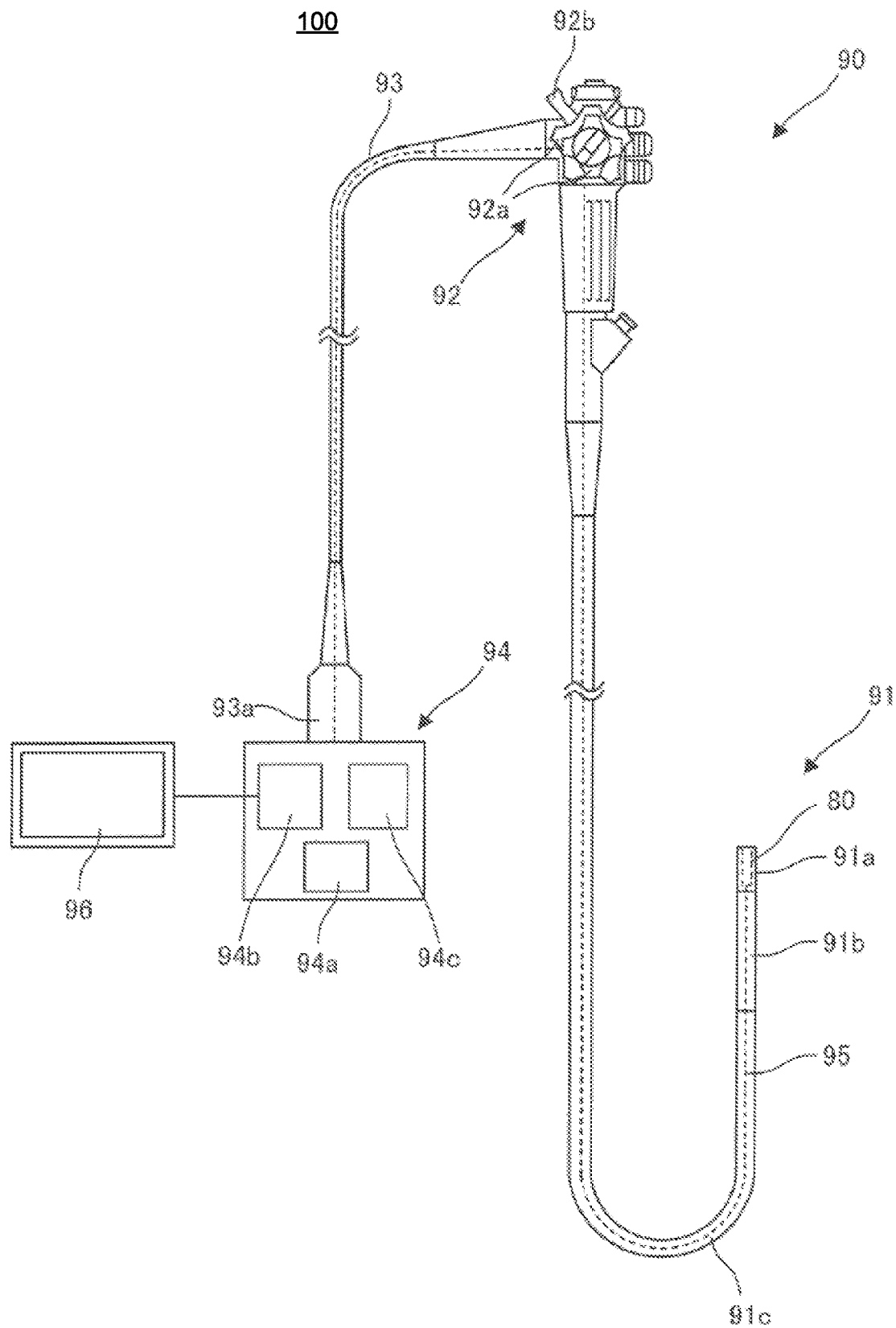
FIG. 28 is a view illustrating a configuration of an endoscope system provided with an endoscope according to a fifth embodiment.

FIG. 28 is a view illustrating a configuration of an endoscope system provided with an endoscope according to a fifth embodiment. An endoscope system 100 illustrated in this drawing is provided with an endoscope 90, a control device 94, and a display device 96.

The endoscope 90 may be introduced into a subject such as a human body and optically captures an image of a predetermined observed region in the subject. Meanwhile, the subject into which the endoscope 90 is introduced is not limited to the human body, but may be another living body or an artificial material such as a machine, a building or the like. In other words, the endoscope 90 may be a medical endoscope or an industrial endoscope.

The endoscope 90 is provided with an insertion portion 91 introduced into the subject, an operating unit 92 located at a proximal end of the insertion portion 91, and a universal cord 93 as a composite cable extending from the operating unit 92.

The insertion portion 91 includes a distal end portion 91a arranged at a distal end, a curving portion 91b which may freely curve arranged on a proximal end side of the distal end portion 91a, and a flexible tube portion 91c having flexibility arranged on a proximal end side of the curving portion 91b to be connected to a distal end side of the operating unit 92. An imaging unit 80 is provided on the distal end portion 91a for condensing light from the subject and capturing an image of the subject. The imaging unit 80 includes an optical unit that condenses the light from the subject and an image sensor that photoelectrically converts the light condensed by the optical unit to output. The optical unit described in any one of the above-describe first to fourth embodiments may be applied to the optical unit. The image sensor is formed of a charge coupled device (CCD) or a complementary metal oxide semiconductor (CMOS). Meanwhile, the endoscope 90 may also be a rigid endoscope without the flexible tube portion 91c included in the insertion portion 91.

The operating unit 92 includes an angle operating unit 92a for operating a curving state of the curving portion 91b, and a zoom operating unit 92b indicating operation of the above-described voice coil motor 10 and performing zoom operation in an optical unit 1, 1A, or 1B. The angle operating unit 92a is formed into a knob shape and the zoom operating unit 92b is formed into a lever shape, but other forms such as a volume switch and a push switch may also be used.

The universal cord 93 is a member for connecting the operating unit 92 to the control device 94. The endoscope 90 is connected to the control device 94 via a connector 93a provided on a proximal end portion of the universal cord 93.

Cables 95 such as a wire, an electric wire, and an optical fiber are inserted through the insertion portion 91, the operating unit 92, and the universal cord 93.

The control device 94 includes a drive control unit 94a that controls the curving state of the curving portion 91b, an image control unit 94b that controls the imaging unit 80, and a light source control unit 94c that controls a light source device not illustrated. The control device 94 including a processor such as a central processing unit (CPU) integrally controls an entire endoscope system 100.

The drive control unit 94a includes an actuator and is mechanically connected to the operating unit 92 and the curving portion 91b via the wire. The drive control unit 94a controls the curving state of the curving portion 91b by moving the wire forward and backward.

The image control unit 94b is electrically connected to the imaging unit 80 and the operating unit 92 via the electric wire. The image control unit 94b performs drive control of a voice coil motor 10 or 10B included in the imaging unit 80 and processing of the image captured by the imaging unit 80. The image processed by the image control unit 94b is displayed on the display device 96.

The light source control unit 94c is optically connected to a light source and the operating unit 92 via the optical fiber. The light source control unit 94c controls brightness and the like of the light source emitted from the distal end portion 91a.

Meanwhile, the operating unit 92 may be formed separately from the insertion portion 91, and the operation of the insertion portion 91 may be performed by remote operation.

Since the endoscope system 100 having the above-described configuration is provided with the imaging unit 80 including the optical unit according to any one of the first to fourth embodiments, this is compact and may rapidly change zoom, so that this is preferably used for capturing a moving image.

Also, in the endoscope system 100, a magnet 12 is provided on a movable portion and a coil 11 is provided on a fixed portion, so that there is no need to move the cable connected to the coil 11. Therefore, there is no possibility that the cable moves to cause disconnection in a limited space of the distal end portion of the endoscope 90, and durability is excellent.

Another Embodiment

Although the modes for carrying out the present disclosure are heretofore described, the present disclosure should not be limited only to the above-described embodiments. For example, the above-described optical unit may further be provided with at least one magnetic detector that detects magnetism and a current control unit that controls current applied to the coil 11 based on a detection result of the magnetic detector. The magnetic detector is realized by using, for example, a Hall element or a magnetoresistance effect element (MR element). The magnetic detector is fixed to a supporting member provided on a radially outer peripheral side of the coil 11. By controlling the current applied to the coil 11 based on the magnetism detected by the magnetic detector, it becomes possible to more precisely control a driving speed and a stop position of the movable portion.

Although the number of magnets arranged in the movable portion is not limited to those described in the first to fourth embodiments, the even number is more preferable.

It is only required that the magnet and the rotation regulating unit may be assembled to the thinned portion provided in the fixed portion, and it is not required that this penetrates to the radially outer peripheral side.

In this manner, the present disclosure may include various embodiments and the like not herein described and design changes and the like may be appropriately made within the scope of the technical idea recited in claims.

According to the present disclosure, downsizing and weight reduction of the actuator for moving the movable lens forward and backward may be realized.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An optical unit comprising:
    a fixed portion having a tubular shape configured to hold at least one of an object side fixed lens group and an image side fixed lens group, the fixed portion including a plurality of thinned portions formed, at a regular interval, at positions symmetrical with respect to a central axis of the tubular shape;
    a movable portion having a tubular shape configured to hold a movable lens group between the object side fixed lens group and the image side fixed lens group, the movable portion being arranged radially inside the fixed portion so as to be slidable with respect to the fixed portion and having a same central axis as the fixed portion; and
    a voice coil motor configured to relatively move the movable portion with respect to the fixed portion in a direction of the central axis, the voice coil motor including
        a coil arranged on the fixed portion, and
        a plurality of magnets arranged on the movable portion so as to be accommodated in the thinned portions of the fixed portion, respectively, the magnets being magnetically polarized in directions orthogonal to the central axis and substantially symmetrical with respect to the central axis,
    wherein at least two magnets adjacent to each other in a circumferential direction in a cross section orthogonal to the central axis out of the plurality of magnets are arranged so as to be shifted in opposite directions in the circumferential direction.

2. The optical unit according to claim 1,
wherein the fixed portion is formed of a material having relative magnetic permeability larger than 1.0.

3. The optical unit according to claim 1,
wherein the coil is wound around the central axis.

4. The optical unit according to claim 1,
wherein the magnets include a plurality of groups of a first magnet and a second magnet arranged side by side in the central axis direction with magnetic polarization directions opposite to each other,
a plurality of first magnets has same magnetic polarization directions,
the coil includes a first coil opposed to the plurality of first magnets and a second coil opposed to a plurality of second magnets and connected to the first coil, and
directions of current flowing through the first coil and the second coil are opposite to each other.

5. The optical unit according to claim 1, further comprising:
a rotation regulating unit configured to regulate rotation of the movable portion about the central axis with respect to the fixed portion.

6. The optical unit according to claim 5,
wherein the rotation regulating unit is located in at least a part of the thinned portions of the fixed portion.

7. The optical unit according to claim 5,
wherein the magnets include a plurality of groups of the first magnet and the second magnet arranged side by side in the central axis direction with the magnetic polarization directions opposite to each other,
the plurality of first magnets has same magnetic polarization directions,
the coil includes the first coil opposed to the plurality of first magnets and the second coil opposed to the plurality of second magnets and connected to the first coil,
the directions of the current flowing through the first coil and the second coil are opposite to each other, and
the rotation regulating unit is arranged between at least one group of the first magnet and the second magnet adjacent to each other in the central axis direction.

8. The optical unit according to claim 5,
wherein a width of the rotation regulating unit in a plane orthogonal to the central axis is larger than a width of the magnet in the plane.

9. The optical unit according to claim 5, wherein at least a portion of the rotation regulating unit, which is in contact with the fixed portion, has a curved shape.

10. The optical unit according to claim 1,
wherein number of the magnets is an even number.

11. An endoscope adapted to be inserted into a subject to observe an inner side of the subject, the endoscope comprising:
the optical unit according to claim 1; and
an image sensor configured to convert light condensed by the optical unit into an electric signal.

* * * * *